United States Patent
Nishida et al.

(10) Patent No.: US 12,298,216 B2
(45) Date of Patent: May 13, 2025

(54) PARTICLE SENSOR AND SENSING METHOD

(71) Applicant: CAMBRIDGE ENTERPRISE LIMITED, Cambridge (GB)

(72) Inventors: Robert Nishida, Victoria (CA); Tyler James Johnson, Edmonton (CA); Simone Hochgreb, Cambridge (GB); Adam Meyer Boies, Cambridge (GB)

(73) Assignee: CAMBRIDGE ENTERPRISE LIMITED, Cambridge (GB)

( * ) Notice: Subject to any disclaimer, the term of this patent is extended or adjusted under 35 U.S.C. 154(b) by 423 days.

(21) Appl. No.: 17/632,013

(22) PCT Filed: Jul. 30, 2020

(86) PCT No.: PCT/GB2020/051820
§ 371 (c)(1),
(2) Date: Feb. 1, 2022

(87) PCT Pub. No.: WO2021/023972
PCT Pub. Date: Feb. 11, 2021

(65) Prior Publication Data
US 2022/0268684 A1    Aug. 25, 2022

(30) Foreign Application Priority Data

Aug. 2, 2019 (GB) .................... 1911091
Dec. 31, 2019 (GB) .................... 1919455

(51) Int. Cl.
*G01N 15/06* (2024.01)
*G01N 1/22* (2006.01)
(Continued)

(52) U.S. Cl.
CPC .......... *G01N 15/0656* (2013.01); *G01N 1/22* (2013.01); *G01N 15/0266* (2013.01);
(Continued)

(58) Field of Classification Search
CPC .. G01N 1/22; G01N 15/0266; G01N 15/0656; G01N 33/0004;
(Continued)

(56) References Cited

U.S. PATENT DOCUMENTS 3,573,460 A    4/1971  Skala
3,735,138 A    5/1973  Rork et al.
(Continued)

FOREIGN PATENT DOCUMENTS

CH    706 903        3/2014
CN    203443878      2/2014
(Continued)

OTHER PUBLICATIONS

"Experimental determination of the steady-state chargin probabilities and particle size conservation in non-radioactive and radioactive bipolar aerosol charges in the size range of 5-40 nm" by Kallinger et al., J Nanopart Res (2015) 17:171 (Year: 2015).*
(Continued)

*Primary Examiner* — Justin N Olamit
(74) *Attorney, Agent, or Firm* — Nixon & Vanderhye P.C.

(57) ABSTRACT

A particle sensor for measuring size and concentration properties of particles in a gas includes a bipolar diffusion charger configured to charge particles within a received gas sample by the collision of the received particles with and transfer of charge from both positive and negative ions concurrently. At least one electrometer detects the charge of received particles thereby charged. The net, positive, negative or total charge on the bipolarly charged particles has a low sensitivity to variations in the absolute rate of charge generation in the bipolar diffusion charger. A sensor for a ratio of ion charge mobilities in a bipolar diffusion charger employs an ion trap between the bipolar diffusion charger and at least one electrometer.

23 Claims, 8 Drawing Sheets

(51) Int. Cl.
  *G01N 15/02* (2006.01)
  *G01N 33/00* (2006.01)
  *G01N 15/00* (2006.01)
  *G01N 15/14* (2006.01)

(52) U.S. Cl.
  CPC .. *G01N 33/0004* (2013.01); *G01N 2001/2223* (2013.01); *G01N 2015/0046* (2013.01); *G01N 2015/1486* (2013.01)

(58) Field of Classification Search
  CPC ... G01N 2001/2223; G01N 2015/0038; G01N 2015/0046; G01N 2015/1486
  See application file for complete search history.

(56) References Cited

U.S. PATENT DOCUMENTS

| | | | |
|---|---|---|---|
| 4,053,776 A | | 10/1977 | Hertzberg et al. |
| 4,435,681 A | * | 3/1984 | Masuda ............... B03C 3/34 |
| | | | 324/459 |
| 4,790,650 A | | 12/1988 | Keady |
| 4,837,440 A | | 6/1989 | Burtscher et al. |
| 5,118,959 A | | 6/1992 | Caldow et al. |
| 5,214,386 A | | 5/1993 | Singer et al. |
| 5,431,714 A | | 7/1995 | Burtscher et al. |
| 5,498,271 A | | 3/1996 | Marple et al. |
| 6,003,389 A | | 12/1999 | Flagan et al. |
| 6,230,572 B1 | | 5/2001 | Pui et al. |
| 6,544,484 B1 | | 4/2003 | Kaufman et al. |
| 6,639,671 B1 | | 10/2003 | Liu |
| 6,781,119 B2 | * | 8/2004 | Smith ............... H01J 49/427 |
| | | | 250/286 |
| 7,549,318 B2 | | 6/2009 | Burtscher et al. |
| 7,812,306 B2 | * | 10/2010 | Fissan ............... B03C 3/47 |
| | | | 250/281 |
| 7,836,751 B2 | | 11/2010 | Marra |
| 8,301,396 B1 | | 10/2012 | Dhanijala et al. |
| 8,607,616 B2 | * | 12/2013 | Marra ............... B03C 3/47 |
| | | | 73/28.02 |
| 8,652,240 B2 | * | 2/2014 | Sugiyama ........ G01N 15/0656 |
| | | | 60/275 |
| 8,752,368 B2 | | 6/2014 | Ante et al. |
| 8,823,384 B2 | | 9/2014 | Matsuoka et al. |
| 9,574,986 B2 | | 2/2017 | Janka |
| 9,726,579 B2 | | 8/2017 | Han et al. |
| 9,726,638 B2 | | 8/2017 | Hwang et al. |
| 9,880,097 B2 | | 1/2018 | Evenstad et al. |
| 10,006,846 B2 | | 6/2018 | Karakaya et al. |
| 10,502,710 B2 | | 12/2019 | Hochgreb et al. |
| 11,703,437 B2 | * | 7/2023 | Rostedt ............ G01N 15/0656 |
| | | | 73/28.01 |
| 2003/0163290 A1 | | 8/2003 | Rosin |
| 2006/0150754 A1 | | 7/2006 | Burtscher et al. |
| 2011/0030451 A1 | | 2/2011 | Roesch et al. |
| 2011/0113854 A1 | | 5/2011 | Kammerer et al. |
| 2011/0216317 A1 | | 9/2011 | Marra |
| 2011/0220811 A1 | | 9/2011 | Dick et al. |
| 2012/0262182 A1 | | 10/2012 | Matsuoka et al. |
| 2012/0304738 A1 | | 12/2012 | Landkammer |
| 2013/0148252 A1 | | 6/2013 | Kulkarni et al. |
| 2014/0069169 A1 | | 3/2014 | Janka |
| 2014/0083167 A1 | | 3/2014 | Liu et al. |
| 2014/0247450 A1 | | 9/2014 | Han |
| 2014/0326873 A1 | | 11/2014 | Kokubo |
| 2014/0339415 A1 | | 11/2014 | Caldow et al. |
| 2014/0352405 A1 | | 12/2014 | Motomura et al. |
| 2015/0008932 A1 | | 1/2015 | Brechtel et al. |
| 2015/0020574 A1 | | 1/2015 | Motomura |
| 2017/0097255 A1 | | 4/2017 | Karakaya |
| 2017/0115251 A1 | | 4/2017 | Hisada et al. |
| 2017/0350862 A1 | * | 12/2017 | Hochgreb ............ B03C 3/47 |
| 2018/0200726 A1 | | 7/2018 | Clavaguera et al. |
| 2018/0200727 A1 | | 7/2018 | Clavaguera et al. |
| 2018/0217046 A1 | | 8/2018 | Marra |
| 2020/0011779 A1 | | 1/2020 | Lavrovsky et al. |

FOREIGN PATENT DOCUMENTS

| | | |
|---|---|---|
| DE | 102 29 411 | 1/2004 |
| DE | 10 2009 046 315 | 5/2011 |
| DE | 10 2010 019 076 | 11/2011 |
| DE | 10 2010 030 634 | 12/2011 |
| DE | 10 2010 064 299 | 7/2012 |
| DE | 10 2013 209 872 | 12/2014 |
| EP | 1 156 320 | 11/2001 |
| EP | 1 655 460 | 5/2006 |
| EP | 1 655 595 | 5/2006 |
| EP | 1 681 550 | 7/2006 |
| EP | 1 924 836 | 5/2008 |
| EP | 2 223 080 | 9/2010 |
| EP | 3 165 898 | 5/2017 |
| GB | 2 346 700 | 8/2000 |
| GB | 2 374 671 | 10/2002 |
| GB | 2 378 510 | 2/2003 |
| GB | 2 416 913 | 2/2006 |
| JP | 2014-10147 | 1/2014 |
| JP | 2017-20802 | 1/2017 |
| WO | 92/10745 | 6/1992 |
| WO | 2006/127803 | 11/2006 |
| WO | 2007/000710 | 1/2007 |
| WO | 2008/107372 | 9/2008 |
| WO | 2009/074910 | 6/2009 |
| WO | 2010/136633 | 12/2010 |
| WO | 2012/022842 | 2/2012 |
| WO | 2012/048308 | 4/2012 |
| WO | 2012/098290 | 7/2012 |
| WO | 2012/127104 | 9/2012 |
| WO | 2012/142297 | 10/2012 |
| WO | 2013/083879 | 6/2013 |
| WO | 2013/121094 | 8/2013 |
| WO | 2013/121095 | 8/2013 |
| WO | 2013/121096 | 8/2013 |
| WO | 2013/121115 | 8/2013 |
| WO | 2013/132154 | 9/2013 |
| WO | 2014/033040 | 3/2014 |
| WO | 2014/198737 | 12/2014 |
| WO | 2019/012185 | 1/2019 |

OTHER PUBLICATIONS

Lee H M et al. "Bipolar diffusion charging for aerosol nanoparticle measurement asing a soft X-ray charger" (J. Aerosol Science, vol. 37, No. 7, Jul. 1, 2005) (17 pages).

Hinds, W. C. (1999). Aerosol technology: properties, behavior, and measurement of airborne particles. John Wiley & Sons. (200 pages).

Pramod Kulkarni, Paul A Baron, and KlausWilleke. Aerosol measurement: principles, techniques, and applications. John Wiley & Sons, 2011. (876 pages).

Richard W. Baldauf, Robert B. Devlin, Peter Gehr, Robert Giannelli, Beth Hassett-Sipple, Heejung Jung, Giorgio Martini, Joseph McDonald, Jason D. Sacks, and Katherine Walker. Ultrafine particle metrics and research considerations: Review of the 2015 UFP workshop. International Journal of Environmental Research and Public Health, 13(11):1-21, 2016 (21 pages).

S Bau, B Zimmermann, R Payet, and O Witschger. A laboratory study of the performance of the handheld diffusion size classifier (DiSCmini) for various aerosols in the 15-400 nm range. Environmental Science: Processes & Impacts, 1(2):261-269, 2015 (10 pages).

M I Mead, O A M Popcola, G B Stewart, P Landsboff, M. Calleja, M Hayes, J J Baldovi, M W McLeod, T F Hodgson, J Dicks, et al. The use of electrochemical sensors for monitoring urban air quality in low-cost, high-density networks. Atmospheric Environment, 70:186-203, 2013 (18 pages).

Wayne R Ott and Hans C Siegmann. Using multiple continuous fine particle monitors to characterize tobacco, incense, candle, cooking, wood burning, and vehicular sources in indoor, outdoor, and in-transit settings. Atmospheric Environment, 40(5):821-843, 2006 (23 pages).

Prashant Kumar, Lidia Morawska, Claudio Martani, George Biskos, Marina Neophyton, Silvana Di Sabatino, Margaret Bell, Leslie

(56) References Cited

OTHER PUBLICATIONS

Norford, and Rex Britter. The rise of low-cost sensing for managing air pollution in cities. Environment International, 75:199-205, 2015 (7 pages).
D B Kittelson, W F Watts, J C Savstrom, and J P Johnson. Influence of a catalytic stripper on the response of real time aerosol instruments to diesel exhaust aerosol. Journal of Aerosol Science, 36(9):1089-1107, 2005 (19 pages).
Christof Asbach, Heinz Kaminski, Daniel Von Barany, Thomas A J Kuhlbusch, Christian Monz, Nico Dziurowitz, Johannes Pelzer, Katja Vossen, Knut Berlin, Silvio Dietrich, et al. Comparability of portable nanoparticle exposure monitors. Annals of Occupational Hygiene, 56(5):606-621, 2012 (16 pages).
Harry J White. Particle charging in electrostatic precipitation. Transactions of the American Institute of Electrical Engineers, 70(2):1186-1191, 1951 (6 pages).
Johan Marra, Matthias Voetz, and Heinz-Jürgen Kiesling. Monitor for detecting and assessing exposure to airborne nanoparticles. Journal of Nanoparticle Research, 12(1):21-37, 2010 (18 pages).
Heejung Jung and David B Kittelson, Characterization of aerosol surface instruments in transition regime. Aerosol Science and Technology, 39(9):902-911, 2005 (11 pages).
M Fierz, C Houle, P Steigmeier, and H Burtscher. Design, calibration, and field performance of a miniature diffusion size classifier, Aerosol Science and Technology, 45(1):1-10, 2011 (11 pages).
Ana Maria Todea, Stefanie Beckmann, Heinz Kaminski, and Christof Asbach. Accuracy of electrical aerosol sensors measuring lung deposited surface area concentrations. Journal of Aerosol Science, 89:96-109, 2015 (14 pages).
H Smith. Human respiratory tract model for radiological protection. ICRP publication 66, vol. 24, Nos. 1-3,1994 (492 pages).
Robert Takeo Nishida, Nene Yamasaki, Mario Anton Schriefl, AM Boies, and Simone Hochgreb. Modelling the effect of aerosol polydispersity on unipolar charging and measurement in low-cost sensors. Journal of Aerosol Science, 2019 (12 pages).
R Niessner. The chemical response of the photo-electric aerosol sensor (PAS) to different aerosol systems. Journal of Aerosol Science, 17(4):705-714, 1986 (10 pages).
Lei Zhou, Rian You, Jiaojie Tan, and Michael R Zachariah. Wavelength-resolved UV photoelectric charging dynamics of nanoparticles: comparison of spheres and aggregates. Aerosol Science and Technology, 47(6):672-680, 2013 (10 pages).
Robert T Nishida, Adam M Boies, and Simone Hochgreb. Measuring ultrafine aerosols by direct photoionization and charge capture in continuous flow. Aerosol Science and Technology, 52(5):546-556, 2018 (12 pages).
Peter Kallinger, Gerhard Steiner, and Wladyslaw W Szymanski. Characterization of four different bipolar charging devices for nanoparticle charge conditioning. Journal of Nanoparticle Research, 14(6):944, 2012 (8 pages).
ISO. BS ISO 15900: 2009 (B) Determination of particle size distribution-differential electrical mobility analysis for aerosol particles, 2009 (66 pages).
NA Fuchs. On the stationary charge distribution on aerosol particles in a bipolar ionic atmosphere. Geofisica Pura E Applicata, 56(1):185-193, 1963 (9 pages).
A Wiedensohler. An approximation of the bipolar charge distribution for particles in the submicron size range. Journal of Aerosol Science, 19(3):387-389, 1988 (3 pages).
Shih Chen Wang and Richard C Flagan. Scanning electrical mobility spectrometer. Aerosol Science and Technology, 13(2):230-240, 1990 (12 pages).
Panich Intra and Nakoro Tippayawong. An overview of unipolar charger developments for nanoparticle charging. Aerosol and Air Quality Research, 11:187-209, 2011 (23 pages).
Heinz Kaminski, Thomas A J Kuhlbusch, Heinz Fissan, Lavanya Ravi, Hans-Georg Horn, Hee-Siew Han, Rob Caldow, and Christof Asbach. Mathematical description of experimentally determined charge distributions of a unipolar diffusion charger. Aerosol Science and Technology, 46(6):708-716, 2012 (9 pages).

G Biskos, K Reavell, and N Collings. Description and theoretical analysis of a differential mobility spectrometer. Aerosol Science and Technology, 39(6):527-541, 2005 (16 pages).
B Grob, H Burtscher, and R Niessner. Charging of ultra-fine aerosol particles by an ozone-free indirect uv photo-charger. Aerosol Science and Technology, 47(12):1325-1333, 2013 (10 pages).
D Matter, M Mohr, W Fendel, A Schmidt-Ott, and H Burtscher. Multiple wavelength aerosol photoemission by excimer lamps. Journal of Aerosol Science, 26(7):1101-1115, 1995 (15 pages).
Benjamin Y H Liu and David Y H Pui. A submicron aerosol standard and the primary, absolute calibration of the condensation nuclei counter. Journal of Colloid and Interface Science, 47(1):155-171, 1974 (17 pages).
Martin Fierz, Dominik Meier, Peter Steigmeier, and Heinz Burtscher. Aerosol measurement by induced currents. Aerosol Science and Technology, 48(4):350-357, 2014 (9 pages).
Hoppel, W. A., & Frick, G. M. (1990). The nonequilibrium character of the aerosol charge distributions produced by neutralizers. Aerosol Science and Technology, 12(3), 471-496, Jun. 8, 2007 (27 pages).
Nishida, R. T., Johnson, T. J., Hassim, J. S., Graves, B. M., Boies, A. M., & Hochgreb, S. (2020). A simple method for measuring fine-to-ultrafine aerosols using bipolar charge equilibrium. ACS sensors, 5(2), 447-453, 2020 (7 pages).
Cooper, D. W.; Reist, P. C. Neutralizing charged aerosols with radioactive sources. J. Colloid Interface Sci. 1973, 45, 17-26 (10 pages).
Liu, B. Y.; Pui, D. Y. Electrical neutralization of aerosols. J. Aerosol Sci. 1974, 5, 465-472, (8 pages).
Shimada, M.; Han, B.; Okuyama, K.; Otani, Y. Bipolar Charging of Aerosol Nanoparticles by a Soft X-ray Photoionizer. J. Chem. Eng. Jpn. 2002, 35, 786-793, (8 pages).
Adachi, M.; Pui, D. Y. .; Liu, B. Y. H. Aerosol Charge Neutralization by a Corona Ionizer. Aerosol Sci. Technol. 1993, 18, 48-58 (12 pages).
Stommel, Y.; Riebel, U. A new corona discharge-based aerosol charger for submicron particles with low initial charge. J. Aerosol Sci. 2004, 35, 1051-1069 (19 pages).
Han, B.; Hudda, N.; Ning, Z.; Kim, H.- J.; Kim, Y.- J.; Sioutas, C. A novel bipolar charger for submicron aerosol particles using carbon fiber ionizers. J. Aerosol Sci. 2009, 40, 285-294 (10 pages).
Kwon, S.; Sakurai, H.; Seto, T.; Kim, Y. Charge neutralization of submicron aerosols using surface-discharge microplasma. J. Aerosol Sci. 2006, 37, 483-499 (17 pages).
De La Verpilliere, J., Swanson, J. J.; Boies, A. M. Unsteady bipolar diffusion charging in aerosol neutralisers: A non-dimensional approach to predict charge distribution equilibrium behaviour. J. Aerosol Sci. 2015, 86, 55-68 (14 pages).
Biskos, G.; Reavell, K.; Collings, N. Unipolar diffusion charging of aerosol particles in the transition regime. J. Aerosol Sci. 2005, 36, 247-265 (19 pages).
Büscher, P.; Schmidt-Ott, A.; Wiedensohler, A. Performance of a unipolar "square wave" diffusion charger with variable nt-product. J. Aerosol Sci. 1994, 25, 651-663 (13 pages).
Flagan, R. C. Differential mobility analysis of aerosols: a tutorial. Kona Powder Part. J. 2008, 26, 254-268 (15 pages).
Gunn, R.; Woessper, R. Measurements of the systematic electrification of aerosols. J. Colloid Sci. 1956, 11, 254-259 (6 pages).
Clement, C.; Harrison, R. The charging of radioactive aerosols. J. Aerosol Sci. 1992, 23, 481-504 (24 pages).
Fissan, H.; Neumann, S.; Trampe, A.; Pui, D.; Shin, W. Nanotechnology and Occupational Health; Springer, 2006; pp. 53-59 (180 pages).
Nishida, R. T.; Boies, A. M.; Hochgreb, S. Modelling of direct ultraviolet photoionization and charge recombination of aerosol nanoparticles in continous flow. J. Appl. Phys. 2017, 121, 023104 (14 pages).
Gopalakrishnan, R.; Thajudeen, T.; Ouyang, H.; Hogan, C. J., Jr. The unipolar diffusion charging of arbitrary shaped aerosol particles. J. Aerosol Sci. 2013, 64, 60-80 (21 pages).
Gopalakrishnan, R.; McMurry, P. H.; Hogan, C. J., Jr. The bipolar diffusion charging of nanoparticles: A review and development of approaches for non-spherical particles. Aerosol Sci. Technol. 2015, 49, 1181-1194 (15 pages).

(56) References Cited

OTHER PUBLICATIONS

Yang, Y.; Yu, T.; Zhang, J.; Wang, J.; Wang. W.; Gui, H.; Liu, J. On the performance of an aerosol electrometer with enhanced detection limit. Sensors 2018, 18, No. 3889 (13 pages).

Intra, P.; Tippayawong, N. Development and evaluation of a Faraday cup electrometer for measuring and sampling atmospheric ions and charged aerosols. Part. Sci. Technol. 2015, 33, 257-263 (8 pages).

Tigges, L.; Jain, A.; Schmid, H.-J. On the bipolar charge distribution used for mobility particle sizing: Theoretical considerations. J. Aerosol Sci. 2015, 88, 119-134 (16 pages).

Leppä, J.; Mui, W.; Grantz, A. M.; Flagan, R. C. Charge distribution uncertainty in differential mobility analysis of aerosols. Aerosol Sci. Technol. 2017, 51, 1168-1189 (19 pages).

Chen, X.; Jiang, J. Retrieving the ion mobility ratio and aerosol charge fractions for a neutralizer in real-world applications. Aerosol Sci. Technol. 2018, 52, 1145-1155 (12 pages).

Wiedensohler, A.; Birmili, W.; Nowak, A.; Sonntag, A.; Weinhold, K.; Merkel, M.; Wehner, B.; Tuch, T.; Pfeifer, S.; Fiebig, M.; et al. Mobility particle size spectrometers: barmonization of technical standards and data structure to facilitate high quality longterm observations of atmospheric particle number size distributions. Atmos. Meas. Tech. 2012, 5, 657-685 (29 pages).

Marjamäki, M.; Keskinen, J.; Chen, D.-R.; Pui, D. Y. H. Performance evaluation of the electrical low-pressure impactor (ELPI). J. Aerosol Sci. 2000, 31, 249-261 (13 pages).

Gopalakrishnan, R.; Meredith, M. J.; Larriba-Andaluz, C.; Hogan, C. J., Jr. Brownian dynamics determination of the bipolar steady state charge distribution on spheres and non-spheres in the transition regime. J. Aerosol Sci. 2013, 63, 126-145 (20 pages).

Wiedensobler, A.; Lütkemeier, E.; Feldpausch, M.; Helsper, C. Investigation of the bipolar charge distribution at various gas conditions. J. Aerosol Sci. 1986, 17, 413-416 (4 pages).

Reischl, G. P.; Mäkelä, J. M.; Karch, R.; Necid, J. Bipolar charging of ultrafine particles in the size range below 10 nm. J. Aerosol Sci. 1996, 27, 931-949 (19 pages).

Nishida. R. T.; Johnson, T.; Boles, A.; Hochgreb, S. Measuring aerosol active surface area by direct ultraviolet photoionization and charge capture in continuous flow. Aerosol Sci. Technol. 2019, 53, 1429-1440 (13 pages).

A Naneos information sheet; Naneos particle solutions gmbh, "Lung deposited surface area". Jul. 5, 2012 (7 pages).

Gunn, R. (1954). Diffusion charging of atmospheric droplets by ions, and the resulting combination coefficients. Journal of Atmospheric Sciences, 11(5), 339-347 (9 pages).

Baxter, K. et al. High sensitivity sensor for continuous direct measurement of bipolar charged aerosols. Electrostatics 2007, J. Phys. Conference Series 142 (2008) 012045 (7 pages).

Joe, Y-H. et al. A Study on Electrical Charge Distribution of Aerosol Using Gerdien Ion Counter. Aerosol and Air Quality Research. vol. 18, Issue 12, Dec. 2018 (8 pages).

Kalon J. et al., A Bipolar Charge Measurement System for Aersol Characterization, IEEE Transactions on Industry Applications, vol. 37, No. 2, Mar./Apr. 2001 (8 pages).

Rich, T. A., Pollak, L. W., & Metnieks, A. L. (1959). Estimation of average size of submicron particles from the number of all and uncharged particles. Geofisica pura e applicata, 44(1), 233-241 (9 pages).

Hoppel, W. A., & Frick, G. M. (1986). Ion-aerosol attachment coefficients and the steady-state charge distribution on aerosols in a bipolar ion environment. Aerosol Science and Technology, 5(1), 1-21 (22 pages).

Vijayakumar, R., & Whitby, K. T. (1984). Bipolar steady state charge fraction of ultrafine aerosols. Aerosol Science and Technology, 3(1), 25-30 (7 pages).

Yli-Ojanpera, J., Ukkonen, A., Jarvinen, A., Layzell, S., Niemela, V., & Keskinen, J. (2014). Bipolar charge analyzer (BOLAR): A new aerosol instrument for bipolar charge measurements. Journal of Aerosol Science, 77, 16-30 (15 pages).

Adachi, M., Okuyama, K., Kozura, H., Kousaka, Y., & Pui, D. Y. H. (1989). Bipolar diffusion charging of aerosol particles under high particle/ion concentration ratios. Aerosol Science and Technology, 11(2), 144-156 (14 pages).

Li, L., & Gopalakrishnan, R. (2021). An experimentally validated model of diffusion charging of arbitrary shaped aerosol particles. Journal of Aerosol Science, 151, 105678 (28 pages).

\* cited by examiner

PARTICLE SENSOR AND SENSING METHOD

This application is the U.S. national phase of International Application No. PCT/GB2020/051820 filed Jul. 30, 2020 which designated the U.S. and claims priority to GB Patent Application Nos. 1911091.5 filed Aug. 2, 2019, and 1919455.4 filed Dec. 31, 2019, the entire contents of each of which are hereby incorporated by reference.

FIELD OF THE INVENTION

The invention relates to the field of particle sensors for measuring size and concentration properties of particles in gases.

BACKGROUND TO THE INVENTION

Aerosols consist of solid or liquid particles suspended in a gaseous medium. Aerosols can adversely affect the climate, environment and human health and are commonly emitted as a byproduct of combustion or industrial processes. Aerosol particles may also be engineered for the production of materials with unique properties. Accordingly, there is a demand for sensors which can reliably measure and characterise aerosols.

One of the primary concerns involving aerosols is the direct health impacts from indoor and outdoor air pollution. It is established that there is a direct relationship between sub 2.5 μm aerosol particulate matter ($PM_{2.5}$) concentrations and all-causes mortality. It is also thought that nano-particles or ultra-fine particles (particles smaller than 100 nm in aerodynamic diameter) may have particular health impacts due to their relatively high number concentration, surface area and potential for deeper penetration into the human lung.

Accordingly, it is desirable to be able to analyse the concentration of aerosol particles in air, taking into account both their number concentration and size. Within the diameter range of about 10 to 400 nm, the lung deposited surface area is roughly proportional to Nd, the first moment of a particle size distribution, where N is the number of particles and d is their diameter. This arises from the fact that, whilst the particle surface area is approximately proportional to $Nd^2$, the probability of particle deposition in the lung for submicron particles is approximately proportional to the reciprocal of their diameter, $d^{-1}$ within the diameter range of about 10 to 400 nm. It is therefore useful to obtain a measurement which is roughly proportional to Nd. For non-spherical particles, mobility-equivalent diameter is an appropriate representation of particle diameter in this discussion.

The present invention relates to the field of particle sensors in which particles are received in a gas sample, electrically charged in an electrical charge conditioning stage, and then analysed by electrometric means.

For example, a known class of sensors charges received particles in a gas so that they become either all positively or all negatively charged via collisions with correspondingly charged gas ions. This is referred to as unipolar diffusion charging, reflecting the fact that the received particles which become charged acquire either all positive or all negative charges. The charges on the particles can then be detected using an electrometer, and arrangements of electrodes have been used to generate controlled electrical fields to select charged particles in different size and/or electrical mobility ranges.

In addition, received particles can be charged using photoelectric ionisation. Again, this provides unipolar (positive) charging of received particles which may subsequently be detected by electrometric means (e.g. a Faraday cage).

Particle sensors based on unipolar diffusion charging or photoelectric charging of received particles are known. However, it is essential that the charging of the received particles is consistent. The rate of generation of charged ions and the time for which the received particles remain mixed with the charged ions may each have a critical effect on measurement accuracy and repeatability. Such devices typically measure currents associated with the product of the number of charges per unit volume and their flow rate, either directly or indirectly via collection, or via charge induction, and so uncontrolled variations in charging lead to errors in measurement. As a result, such devices require methods of generating ions which are often expensive and/or bulky, and in which the total charge concentration depends on the details of the particular hardware used to produce the charges. Devices based on unipolar charging are also known to output a current which departs somewhat from Nd, the first moment of particle size distribution, for example some devices output a current which is closer to $Nd^{1.1}$ (proportional to diameter, d, to the power of 1.1).

The invention seeks to provide a particle sensor which is reliable, relatively simple and/or low cost, and which provides a particle measurement which is useful for environmental monitoring. Some unipolar chargers may in fact generate ozone or otherwise be environmentally deleterious and the invention also seeks to avoid this.

The invention makes use of bipolar diffusion charging, a process in which a mixture of positive and negatively charged ions is formed in a gas, typically air. Received particles then acquire positive and negative charges concurrently as a result of collision with these ions.

Bipolar diffusion charging is used in everyday smoke detectors. In those devices, the positively and negatively charged ions are generated by radiation from a suitable radioactive material which charges clean air in a reference cell, and surrounding air and any surrounding particles in a sample chamber. The movement of the resulting ions along a potential gradient enables a current to pass between opposing electrodes associated with the reference and sample chamber. Smoke particles block the passage of ions, reducing the current, so that a decrease in current is indicative of the presence of smoke particles. The smoke particles are thereby detected indirectly, and not by direct electrometric measurement of charge on the smoke particles.

Bipolar diffusion chargers are used in scanning mobility particle sizers (SMPS). In these devices, received particles within a specific electrical mobility range are selected using a differential mobility analyser and detected by a condensation particle counter. These devices can be very accurate and provide detailed particle size information, but are expensive and complex. The bipolar diffusion charger is used as a charge neutraliser, designed to reduce any residual charges in the particle stream to a known steady state value. In the bipolar diffusion charging process, both positive and negative ions (charged gas molecules) briefly contact and transfer charge to the received particles.

SUMMARY OF THE INVENTION

According to a first aspect of the invention, there is provided a particle sensor comprising an inlet for receiving a gas sample for analysis, a bipolar diffusion charger configured to charge particles within the received gas sample by the collision of the received particles with and transfer of charge from both positive and negative ions concurrently, and at least one electrometer configured to detect the charge of received particles thereby charged.

The at least one electrometer may be configured to detect the charge of some or all of the received particles thereby charged. Typically, the particle sensor further comprises a circuit configured to receive signals from the at least one electrometer and calculate at least one parameter of the concentration and/or size of the received particles in the received gas sample. The circuit may comprise a hardware processor.

A mixture of received particles and positive and negative ions is formed within the bipolar diffusion charger. The bipolar diffusion charger typically comprises a chamber within which the mixture of received particles and the positive and negative ions is formed. The received gas sample may flow through the chamber. The positive and negative ions may be generated within the chamber. The positive and negative ions may be generated outside the chamber, such as in a separate chamber (e.g. an ion generation chamber), and pass into the chamber, for example by convection or electrostatic forces (e.g. through a conduit).

The bipolar diffusion charger may comprise a radioactive material, such as Americium-241, and a gas, such as air, which is typically the received gas sample. In such chargers, radiation from the radioactive material (alpha particles in the case of Americium-241) collides with gas molecules and creates both positive and negative gas ions within the gas concurrently. However, the bipolar diffusion charger may be based on another principle. For example, the bipolar diffusion charger may comprise an x-ray source or even two unipolar chargers of opposite polarity which charge the same volume of gas concurrently.

The positive and negative ions are gas ions. The ions are formed by ionisation of gaseous molecules within the chamber of the bipolar diffusion charger or elsewhere. There are typically an equal number of positive and negative ions produced during formation of the ions therefore the gas retains an overall neutral charge. The gas retains an overall neutral charge or nearly neutral charge in the bipolar diffusion charger, a charger used to charge particles. The positive and negative ions diffuse within the gas, and are affected also by electrostatic forces, and so collide with and transfer charges to the received particles within the bipolar diffusion charger. The received particles acquire a range of charges which, once a steady state is reached, are as described originally by N. A. Fuchs in 1963 (Geofisica pura e applicata, September 1963, Vol. 56, Issue 1, pp. 185-193). Under collisional equilibrium conditions the particles each have charges which are an integer multiple of e (the electrical charge of an electron), with the majority usually in the range −10e to 10e or −5e to 5e. Typically, a large fraction of particles remain neutrally charged. This steady state arises from a process of charging and discharging of particles via ions of both polarities. When a steady state is reached, the rate of positive charge transfer to particles with q charges to reach q+1 charges is equal to the reverse rate of negative charge transfer to particles with q+1 charges to reach q charges. With ions of only one polarity, a steady state would not be reached. Without wishing to be bound to particular terminology to describe the bipolar charging process, this steady-state process and charge distribution is often referred to as an equilibrium process and/or charge distribution by a person skilled in the art. Although this is a misnomer, the term equilibrium, and terminology with similar meaning, is often used in literature and by those skilled in the art, and thus is also used in this work.

We have found that once a steady state is reached, bipolar diffusion chargers leave particles with a slight overall charge, typically (e.g. in air) a negative charge. Without wishing to be bound by theory we believe that this results from the higher mobility of the negative ions relative to positive ions. This means that the charge on the bipolar charged received particles can be detected with an electrometer without requiring to separate the positive and negative charged received particles. Accordingly, some aspects of the invention measure the net charge of received particles thereby charged, i.e. the difference between the total positive charge and total negative charge of received particles thereby charged.

Whereas the resulting charge distribution as a function of particle diameter has been predicted since 1963, this has only recently been measured in detail. Further, we have observed experimentally that the net charge measured is very stable and is insensitive to variations in the rate of charge generation within the bipolar diffusion charger. Thus, it is not necessary to measure the rate of charge generation within the bipolar diffusion charger or to control for variations with time in charge generation or the residence time of the received particles in a charging zone, provided that these parameters exceed at least a minimum threshold. As a result, the received particles can be charged such as to be suitable for detection with an electrometer reliably in a simple device.

The overall net charge at steady state arises from the different mobility of the positive and negative ions (in particular the higher mobility of negative ions relative to positive ions when the bipolar diffusion charger uses air as the source of positive and negative ions). The charging of the received particles by a bipolar diffusion charger moves towards a steady state. The person skilled in the art can specify a bipolar diffusion charger which is sufficiently effective to ensure that charging is close to steady state and we have found that typical radiation sources used in domestic smoke alarms have more than sufficient activity for use in the detection of typical levels of aerosols in urban environments. It may be that a steady state is reached. Nevertheless, this is not essential, and it may be that a steady state is not reached.

The mean net charge on bipolarly charged particles at steady state is proportional to the first moment of the particle diameter distribution, Nd, where N is a numerical count per unit volume and d is the particle diameter, over at least the range of 50 to 1000 nm diameters. Accordingly, the current measured by the at least one electrometer is approximately a measurement of the product of the number of particles to be detected by the electrometer per second and the mean net charge of those particles. Typically, the circuit divides the measured current by a measured or known air volume flow rate, giving a first moment of charge. When the received particles are in a size range of about 10 to 400 nm this first moment of charge measurement is proportional to the lung deposited surface area (LDSA) concentration (LDSA per unit volume of gas) of the received particles in the received gas sample which, as described above, is a very relevant measurement.

The at least one electrometer will typically also measure the charge of any remaining free ions which have been mixed with the received particles in the bipolar diffusion charger, if present. Although not essential it would be preferable to remove remaining free ions so that the at least one electrometer measures charges only from the received particles thereby charged.

Accordingly, the particle sensor typically comprises an ion trap between the bipolar diffusion charger and at least one said electrometer (at least one, or each, electrometer of the said at least one electrometer), configured to separate free (e.g. flowing) positive and negative ions mixed with the received particles in (e.g. the chamber of) the bipolar diffusion charger) from the received particles before they reach at least one said electrometer. Thus free positive and negative ions (generated by the bipolar diffusion charger or found in the initial gas sample) are separated from a mixture of these ions with the received gas and the received particles (some of which will be charged and some of which will be uncharged). Thus, the ion trap is typically downstream of the bipolar diffusion charger and upstream of at least one said electrometer (where downstream refers to further along a gas flow path from an inlet through the bipolar diffusion charger to the at least one electrometer and upstream refers to the opposite direction). The ion trap typically removes the free positive and negative ions (generated by the bipolar diffusion charger), which have been mixed with the received particles, from the received particles (whether charged or uncharged) before the received particles (whether charged or uncharged) reach at least one said electrometer. Very small (<5 nm) received particles may also be removed, but larger received particles will remain in the flow.

Thus, at least one said electrometer can accurately quantify the charge of the particles (without being affected by the charge of the free ions). The ion trap may comprise a pair of spaced apart electrodes, which are oppositely charged during use. They may be spaced apart within (e.g. located on opposite walls of) a chamber or tube through which gas passes between the bipolar diffusion charger and the at least one electrometer. Nevertheless, the ion trap may have a different form, for example it may comprise an ion selective filter membrane. It may be that the current generated from the capture of ions at either of the spaced apart electrodes is not used to determine an output of the sensor (and typically is not measured). However, in some embodiments, the current generated from the capture of ions at either of the spaced apart electrodes is measured and the controller processes the current to determine one or more parameters of the charge flux (for example parameters of the charge generation) in the bipolar diffusion charger, or to detect an excess of particles, for example to detect smoke in the event of a fire.

Advantageously, the current at the ion trap need not be monitored. Nevertheless, the ion trap may also comprise an electrometer, in which case there is at least one further electrometer (downstream of the ion trap). In this case the at least one electrometer may comprise an electrometer associated with the ion trap and one or more electrometers which are downstream of the ion trap. The at least electrometer may be one or more electrometers, for example an electrometer associated with the ion trap and one or more further electrometers.

It may be that the ion trap is configured to separate the ions from the mixture of gas and received particles by diffusion. They make use of the much higher diffusion coefficient of the gas ions of the bipolar diffusion charger than the received particles. A simple example would be a tube formed of material which is porous to ions through which the mixture flows. Ions may diffuse out through the walls of the tube while the received particles would more closely follow a flow path through the tube and so be less likely to be lost to the walls of the tube. Alternatively, another simple example would be a tube formed of electrically conductive material through which the mixture flows. Ions may diffuse to, collide with, and transfer charge to the walls of the tube which would conduct away the electrical charge from the ions.

It may be that there is a conduit between the bipolar diffusion charger and the ion trap. The received particles and the ions may flow together through the conduit. The additional time required for the received particles to pass through the conduit mixed with positive and negative ions facilitates equilibration between the particles and ions in the gas.

One or more or all of the electrometers may be a charge-summing detector. They produce an output which is dependent on (typically proportional to) the sum of the charge per unit time which is detected by the one or more electrometers (current).

One or more or all of the electrometers may for example comprise a Faraday cup or a wire grid.

It may be that the one or more electrometers measure the current produced by all of the particles which have been received through the inlet and charged by the bipolar diffusion charger.

Typically, the resulting particles are measured by the at least one electrometer without positive and negatively charged received particles being separated from each other. Thus the charged particles received and measured by the at least one electrometer typically comprise a mixture of positively, negatively and neutrally charged particles, with a net overall charge (typically a net overall negative charge). Typically, the particles which are received, bipolarly charged and measured by the at least one electrometer concurrently have a wide range of particle mobilities (i.e. mobility diameters), for example, particle mobilities varying by a factor of at least 10. In contrast to a SMPS device which selects a narrow range of particle mobilities at a time, the sensor typically does not include a differential mobility analyser and/or a condensation particle counter. Omitting separation of the received particles by charge or mobility can keep the device simple and low cost. Nevertheless the particle sensor, such as the first example of the sensor, could be used in combination with a particle counter (which derives N, the number of particles) which could be divided into the output of the circuit/measured current to obtain an estimate of mean particle diameter (which can be expressed as an estimate of mean particle mobility diameter or geometrical diameter as required). Other embodiments of the particle sensor, such as the second example of the sensor, can independently obtain an estimate of both the number of particles (N) and mean particle diameter (d).

Still further, as well as the net charge, the distribution of particle charges arising from bipolar diffusion charging that achieves steady state is also stable and insensitive to variations in the rate of charge generation within the bipolar diffusion charger. In some embodiments, some or all of the positively charged particles and/or some or all of the negatively charged particles are separated from particles of different polarity and/or separated from particles of the opposite polarity and/or separated from the other particles which were exposed to ions from the bipolar diffusion charger, and the charge of the separated particles is measured. As explained further on, this segregation can yield a larger signal and/or a signal which is less sensitive to variations to the mobilities of charging ions than other embodiments, such as the net aerosol current. Such embodiments may also generate different or multiple measurement signals, thus allowing the particles to be further characterized.

By separating some or all of the positively and/or negatively charged particles from particles of opposite polarity we refer to separating some or all of the positively charged particles from negatively charged particles, and optionally also from neutrally charged particles, and/or separating some or all of the negatively charged particles from positively charged particles and optionally also from neutrally charged particles.

By separating some or all of the positively and/or negatively charged particles from particles of different polarity we refer to separating some or all of the positively charged particles from both negatively and neutrally charged particles and/or separating some or all of the negatively charged particles from both positively and neutrally charged particles.

Thus, it may be that the received particles thereby charged (i.e. after charging by the bipolar diffusion charger) are separated by charge polarity, typically using a potential gradient formed between two or more electrodes, prior to or during the step of charge measurement by at least one said electrometer.

The separation is by charge polarity, rather than by particle diameter. Thus, measurements of the charge of only positive charged particles and/or only negatively charged particles, from the received particles which have been charged by the bipolar diffusion charger may be obtained. Even after separation by polarity, the particles will typically have a wide range of particle mobilities (i.e. mobility diameters) and/or electrical mobilities (i.e. electrical mobility diameters), for example, the separated particles may have particle mobilities and/or electrical mobilities varying by a factor of at least 5, or at least 10.

More generally, some or all of the received particles of the same polarity thereby charged (i.e. after charging by the bipolar diffusion charger), may be separated from particles of different and/or opposite polarity. For example, all positively charged particles, or at least positively charged particles with electrical mobilities higher than a threshold may be separated from other particles and/or all negatively charged particles, or at least negatively charged particles with electrical mobilities higher than a threshold may be separated from other particles. Typically, in this case, positively charged particles with electrical mobilities higher than the threshold or negatively charges particles with electrical mobilities higher than the threshold are separated out. The separation functions each act as a low pass filter in terms of particle electrical mobility (whereby the particles which have an electrical mobility higher than the threshold are detected (and typically also captured), whilst the remainder are not detected (and typically pass through the device). Thus the separation is typically not a band pass filter which selects particles in a band of electrical mobilities.

The separation of particles by charge polarity may take place before, after or during the step of removing free ions using the ion trap, where the ion trap is present. Measurements are thereby obtained of the sum of the charge of the separated positively charged particles and/or the sum of the charge of the separated negatively charged particles. The sums of charges are typically expressed as currents.

Thus, in these embodiments, at least one electrometer measures the charge of only positively charged or only negatively charged particles, rather than the net charge of the unseparated mixture of positively and negatively charged particles (although this net charge may also be measured).

Counterintuitively, although the focus is no longer on the small (typically negative) net charge of particles which have been subject of the equilibrium processes of bipolar diffusion charging, we have found that the sum of positive charges and/or the sum of negative charges of particles thereby produced, individually and in combination (summing the absolute value of the sum of positive charges and the absolute value of the sum of negative charges), gives larger signals and/or more information, while still benefiting from bipolar diffusion charging being an equilibrium process which is relatively insensitive to variations in the rate of charge generation within the bipolar diffusion charger. In these embodiments, the measured current of only positively charged particles, only negatively charged particles, or the combination of these (for example the sum of the absolute values of the current of the positively charged particles and the current of the negatively charged particles, referred to herein as the total aerosol current) is less sensitive to variations to the ion-mobility ratio than other embodiments, such as the net charge of unseparated positively charged and negatively charged particles (referred to herein as the net aerosol current). In examples, changing the ion mobility ratio from 0.875 to 0.795 changes the net aerosol current by 72% on average for particles from 2 to 903 nm, however the same ion mobility ratio change affects the total aerosol current by only 3% on average.

The separation may result in a stream of positively charged particles and/or a stream of negatively charged particles, from the received particles which have been charged by the bipolar diffusion charger. The separated positively charged and/or negatively charged particles may be some or all of the positively charged and/or negatively charged particles which have been charged by the at least one bipolar diffusion charger. In this case, at least one electrometer is configured to detect the charge of the positively charged particles and at least one electrometer is configured to detect the charge of the negatively charged particles. The stream of positively charged particles and the stream of negatively charged particles may be separate and their charges may be detected by separate electrometers. However, it may be that a stream of positively charged particles and a stream of negatively charged particles are generated alternately. In this case, the charge of each may be detected by the same (or different) one or more electrometers.

It may be that one or more electrometers is configured to both separate the positively and/or negatively charged particles from particles of different and/or opposite polarity and to (independently) measure the charge of the (thereby separated) positively charged particles and/or the negatively charged particles.

It may be that one or more electrometer comprises first and second electrodes and is configured to apply a positive potential to the first electrode and a negative potential to the second electrode, to thereby attract the positively charged particles, of the received charged particles, to the second electrode and the negatively charged particles, of the received charged particles, to the first electrode, to thereby separate the positively charged particles and the negatively charged particles, and further comprises at least one current sensor to measure the current of negative charges received at the first electrode and/or the current of positive charges received at the second electrode. Thus, an electrometer may be configured to both separate the positively and negatively charged received particles (which have been charged by the bipolar diffusion charger) and to independently determine the charges of the positively charged particles and the negatively charged particles. Note that it is possible to independently determine the charges of the positively charged particles and the negatively charged particles by for example measuring the sum of the magnitude of the charges of the positively charged particles and the magnitude of the charges of the negatively charged particles, and also by measuring the difference between the magnitude of the charges of the positively charged particles and the magnitude of the charges of the negatively charged particles. It is therefore not essential to explicitly measure the charges of the positively charged particles and the negatively charged particles as such.

The circuit may calculate the at least one parameter of the concentration and/or size of the received particles in the received gas sample taking into account one or more of:
(i) the measured charges (typically current) of the separated positively charged particles;
(ii) the measured charges (typically current) of the separated negatively charged particles;
(iii) the sum of the absolute value of the measured charges (typically sum of the charges) of the separated positively charged particles and the separated negatively charged particles (i.e. $abs[i_+]+abs[i_-]$ where $i_+$ is the current arising from the detected positively charged particles and $i_-$ is the current arising from the detected negatively charged particles); and
(iv) the net charges (typically current) of the positively and negatively charged particles ($abs[i_+]-abs[i_-]$), which corresponds to the signal obtained by measuring the net charge of unseparated charged particles.

The sum of the absolute value of the measured charges, $abs[i_+]+abs[i_-]$ (the "total aerosol current") can be substantially greater that the net charge, $abs[i_+]-abs[i_-]$ (the "net aerosol current"). Furthermore, due to the equilibrium processes of bipolar diffusion charging, this sum is relatively insensitive to changes in the parameters of the bipolar diffusion charger.

The circuit may independently calculate the total number concentration and average size of particles in the received particles from two or more of measurements (i)-(iv) above. This is possible as two or more independent signals are processed.

The circuit may calculate the lung deposited surface area of the received particles, typically based on measurement (iv), or two or more of measurements (i)-(iii).

The circuit may calculate the ion mobility ratio of the bipolar diffusion charger from two or more of measurements (i)-(iv) above and/or an ion trap current, while measuring particles of known or measured size or concentration, and use these measurements as a calibration parameter. There is therefore one fewer unknown than is required to determine the ion mobility ratio if only the net aerosol current (net current of unseparated positive and negatively charged particles) is measured.

In any of the embodiments, the one or more electrometers may be flow-through electrometers, which measure charge in gas (e.g. air) passing through the electrometer. The particles may be retained within the electrometer. The particle sensor may be a flow-through sensor. The particle sensor may comprise a body defining the inlet and typically also an outlet.

The particle sensor may comprise or be used with an air flow speed sensor. The sensor may comprise or may be used with, an air flow regulator, such as a fan or an air pump, to regulate the speed at which received particles are charged and passed through the electrometer. This enables measurements per unit volume to be calculated. Alternatively, the sensor may comprise, or be used with an air speed sensor (which may function by detecting the speed at which received particles move through the sensor, for example, optically), to thereby enable measurements per unit volume of air to be made. This may enable an air flow regulation device to be omitted giving a simpler device. Air may flow through the device by convection. It is possible for the device to have an inlet but no outlet and to be based on diffusion.

It may be that the received particles are aerosols. It may be that the received particles have a diameter of at least 10 nanometers. It may be the received particles have a diameter of at least 50 nanometers. It may be that the received particles comprise $PM_{2.5}$. The received particles may be particulates. The received particles may be particulate matter. It may be that the received particles comprise or are soot particles.

Typically, the bipolar diffusion charger comprises an amount of a radioactive element with an activity of at least 5 kBq. It may be that the bipolar diffusion charger comprises an amount of a radioactive element with an activity of less than 500 kBq or less than 50 kBq. Americium-241 sources with an activity in the range of 5 to 50 kBq are in common use in smoke detectors and do not require special handling procedures for consumers.

It may be that the gas molecules which are charged by the bipolar diffusion charger are received with the gas sample, for example they may be air molecules where the gas sample is a sample of atmospheric air. However, it may be that the bipolar diffusion charger comprises an ionisable material, typically a solid, which is ionised within the bipolar diffusion charger. The ionisable material may be a material which is ionisable by radiation, typically by radiation from the radioactive material, where present. The ionisable material may be a gas or a solid or a liquid sacrificial material, which is typically stationary. The ionisable material may be located within the bipolar diffusion chamber and/or within a chamber containing the radioactive material. The ions formed in the bipolar diffusion charger may come at least in part from the ionisable material. This enables the mobility of ions within the bipolar diffusion charger to be regulated. The ionisable material may comprise a salt, for example sodium chloride. The ionisable material may be a siloxane. It is also possible that one or more chargeable gaseous species are introduced into the bipolar diffusion charger, either as part of the gas sample (for example introduced into the gas sample) or separately. Again, this enables the mobility of ions within the bipolar diffusion charger to be regulated, for example to maximise the ratio of the mobility of ions of one polarity to ions of the other polarity or to optimise the consistency of charging or the speed of reaching a steady state (equilibrium). In either case, this can enable the overall net magnitude of the charging of the received particles to be regulated, and potentially even for the overall charge to be positive rather than negative (for example where positive gaseous ions are more mobile than negative ions). The sensor may comprise or be used with a temperature regulator (e.g. one or more heating or cooling elements) to regulate the temperature of gas within the bipolar diffusion charger (for example to heat or cool the gas, or to obtain a target temperature). This may enable ion mobility to be regulated or independently, this may be used to increase the electrometer current since electrometer current proportional to the net charge on the particles is a linear function of temperature as can be seen from Equation 7. The sensor may also comprise or be used with a humidity regulator to regulate the humidity of gas within the bipolar diffusion charger (typically by regulating the humidity of gas upstream of the bipolar diffusion charger).

One or more electrical fields may be applied within the bipolar diffusion charger (using a plurality of electrodes) to enhance bipolar diffusion charging, for example by attracting the ions of the bipolar diffusion charger towards the received particles or vice versa. Bipolar diffusion charging may also be enhanced by advection, for example using an air flow generator configured to generate advection within the sensor.

An advantage of the invention is that the net, positive, negative or total charge on the bipolarly charged received particles has a low sensitivity to variations in the absolute rate of charge generation in the bipolar diffusion charger. It may be that parameters of charge flux of ions within the bipolar diffusion charger are not measured. It may be that the rate of charge generation within the bipolar diffusion charger is not measured. Nevertheless, in some embodiment, parameters of charge flux of ions within the bipolar diffusion charger (e.g. the rate of charge generation) may be measured. The sensor may comprise a current sensor configured to measure the current which flows between oppositely charged electrodes in the ion trap. The measured current may be processed and compared with a threshold indicative of a predetermined acceptable rate of charge generation. The measured current may be processed to determine one or more properties of the particle concentration and/or size. The processing may also take into account the at least one electrometer current used to measure mean particle charge, or the efficiency of the ion source or properties of the ions and may take into account the at least one electrometer current (used to measure mean particle charge/the first moment of particle size distribution).

It may be that the rate of charging of gas molecules by the ion source, or the absorbance of ions by the ion trap, is modulated, for example on or off. Thus, the one or more electrometers will output a modulated signal. The measurement from one or more electrometers may be (correspondingly) demodulated (i.e. the underlying unmodulated signal may be extracted from the modulated signal). This reduces the effects of an offset, thereby accounting for signal drift over time. Modulation may also be used to quantify signal drift. In order to modulate the rate of charging of gas molecules, it may be that a radiation source is moved, or a cover for the radiation source is moved (e.g. a shutter opened and closed), or an electric field which regulated the movement of generated ions is modulated. In order to module the absorbance of ions by the ion trap, the potential difference between electrodes within the ion trap may be modulated (e.g. switched on and off). Modulation may also reduce clogging of the device with received particles.

According to a second aspect of the invention there is provided a method of measuring a parameter of the size and/or concentration of particles in a gas sample for analysis, the method comprising the steps of receiving a gas sample comprising particles, charging received particles in the gas sample by bipolar diffusion charging thereby charging the particles by the collision of received particles with and the transfer of charge from both positive and negative ions concurrently, and using at least one electrometer to detect the net charge of received particles which are thereby charged.

Bipolar diffusion charging creates a mixture of positive and negative ions (charged gas molecules). The positive and negative ions may be generated by collisions between molecules and radiation (typically alpha or beta particles) from a radioactive material. In the present conception of the device, the positive and negative ions consist of gas molecules (typically gas molecules within the received sample) although in some embodiments a solid, gas or liquid material (which is typically present in or introduced into the bipolar diffusion charger) may be ionised.

The received particles (received in the gas sample, which may be drawn into the sensor) are charged by transfer from the resulting positive and negative ions. Positive and negative ions are both present and so collisions with and transfer of charge from both positive and negative ions (to received particles) takes place concurrently. This arises as the received particles collide with the positive and negative ions. Typically, the charging of the received particles by the positive and negative ions is an equilibrium process. It may be that the charging does, or in some embodiments does not, reach a steady state (equilibrium). As a result of the charging, the received particles have a distribution of charges, with a net charge, which is typically a net negative charge.

Typically, the method comprises separating the received particles (which have passed through the bipolar diffusion charger) from the free positive and negative ions (formed during bipolar diffusion charging, e.g. from collisions between gas molecules and radiation), passing the received particles and said free positive and negative ions through an ion trap which removes the positive and negative ions, before the received particles reach at least one said electrometer. The method typically comprises separating free (e.g. remaining) positive and negative ions from the mixture of received particles and positive and negative ions formed during bipolar diffusion charging. The positive and negative ions may be removed (from the received particles) before the received particles reach the or each of the at least one electrometer, although it is possible for the ion trap to comprise an electrometer, in which case the at least one electrometer comprises an electrometer associated with the ion trap and at least one further electrometer (downstream of the ion trap). Accordingly, typically a mixture of received particles and positive and negative ions is formed in the bipolar diffusion charger (e.g. in a chamber of the bipolar diffusion charger) and the ion trap typically separates free positive and negative ions in this mixture (e.g. which remain in the flow) from the received particles, before the received particles reach at least one said electrometer. Thus, the ions are typically removed by the ion trap and the charge of the received particles is detected by at least one said electrometer (downstream of the ion trap).

The received particles may be separated from the positive and negative ions by an electrical potential gradient applied between electrodes. Although a benefit of the invention is that it is not essential to monitor charge generation, in some embodiments the current generated from the capture of ions at the electrodes is monitored to measure the rate of ionisation or to detect the presence of an amount or size of particles exceeding a threshold or to detect smoke (from a decrease in the current between the electrodes which exceeds a threshold). It is possible for the received particles to be separated from free positive and negative ions by other means, for example by diffusion separation if the received particles are sufficiently large (for example greater than approximately 50 nm in diameter).

One or more electrometers may be a charge summing electrometer. One or more electrometers may output a current related to (typically proportional to, for example equal and opposite to) the rate of charge flow into or through the electrometers. One or more electrometers may measure the rate of charge flow into or through the electrometers.

The method may comprise directing the received particles and the ions through a conduit, before they are separated (e.g. by the ion trap) to provide time for equilibration.

The flow of gas through bipolar diffusion charging to the one or more electrometers may be regulated by an air flow regulator (e.g. a fan). The method may comprise measuring air flow speed. The output from the one or more electrometers may be processed to estimate a parameter relating to the number and size of the received particles, typically per unit volume of the received air sample. The output may be processed to estimate a first moment of the particle size distribution in the received air sample. The output may be processed to estimate a lung deposited surface area concentration.

The method may include a step of modulating the removal of positive and negative ions from the charged received particles (for example modulating the potential different between said electrodes) or modulating the generation of the positive and negative ions, and demodulating the current measured by the one or more electrometer to improve an estimate of the current of charged received particles flowing into the one or more electrometer.

In some embodiments, the method comprises separating the positively charged particles from the negatively charged received particles, both of which have been charged by the bipolar diffusion charger, and determining the charge of the positive charged particles and/or the negative charged particles (with one or more electrometers). The method may comprise separating some or all of the positively or negatively charged received particles which have been charged by the bipolar diffusion charger from particles of different and/or opposite polarity. The charged received particles (which have passed through the bipolar diffusion charger) may be separated from the free positive and negative ions before, during or after separation of the positively or negatively charged received particles from the particles of different and/or opposite polarity.

It may be that the received particles are separated by a potential difference applied between two electrodes, and the current at each electrode is measured thereby providing a signal which is a measurement of the charges of the positively charged particles and a signal which is a measurement of the charges of the negatively charged particles.

The method may comprise measuring one or more of:
(i) the sum of the charges (typically current) of the separated positively charged particles;
(ii) the sum of the charges (typically current) of the separated negatively charged particles;
(iii) the sum of the absolute value of the charges (typically sum of the charges) of the separated positively charged particles and the separated negatively charged particles (i.e. $abs[i_+]+abs[i_-]$ where $i_+$ is the current arising from the detected positively charged particles and $i_-$ is the current arising from the detected negatively charged particles); and
(iv) the net charges (typically current) of the positively and negatively charged particles ($abs[i_+]-abs[i_-]$), which corresponds to the signal obtained by measuring the net charge of unseparated charged particles.

The method may comprise independently measuring the number concentration and average size (e.g. diameter) of the received particles from two or more of the above measurements (i) to (iv).

The method may comprise calculating the ion mobility ratio of the bipolar diffusion charger from two or more of measurements (i)-(iv) above and/or an ion trap current, while measuring particles of known or measured size or concentration, and use these measurements as a calibration parameter.

Typically, the measured charge of the separated positively charged particles is the charge of positively charged particles of a range of charges and sizes (optionally all positive charges) and the measured charge of the separated negatively charged particles is the charge of a negatively charged particles of a range of charges and sizes (optionally all negative charges). Typically, the positively charged particles are not subdivided by charge or particle mobility above the threshold and the negatively charged particles are not subdivided by charge or particle mobility above the threshold. The threshold may be determined by selecting the potential difference used to separate the some or all positively or negatively charged particles from particles of different and/or opposite polarity.

Typically, the particles are separated by polarity without using a sheath flow of particle-free air. Typically, the particles which are separated by polarity are captured.

Typically, the particles that are captured generate the measurement signal, or are used to measure the ratio of ion charge mobilities (not the ones that remain uncaptured).

Features described above in respect of the first or second aspect of the invention are optional features of both the first and second aspects of the invention.

The particles sensing apparatus may also be useful to measure the ratio of ion charge mobilities ($Z_+/Z_-$) in a bipolar diffusion charger. The logarithm of the ratio of ion charge mobilities is proportional to the measured net current of the all of the charged particles and inversely proportional to the temperature, volumetric flow rate of the gas, and first moment of particle size distribution. In more detail, the measured net current is related to the ratio of ion charge mobilities by equation 7 below. The apparatus of the first aspect may be used as a sensor for the ratio of ion charge mobilities in a bipolar diffusion charger.

Accordingly, in a third aspect of the present invention there is provided a sensor for the ratio of ion charge mobilities in a bipolar diffusion charger, the sensor comprising an inlet for receiving a gas sample for analysis, a bipolar diffusion charger configured to charge particles within the received gas sample by the collision of received particles with and transfer of charge from both positive and negative ions concurrently, and at least one electrometer configured to detect the charge of particles thereby charged. Typically, the sensor further comprises a circuit configured to receive signals from the at least one electrometer and calculate at least one parameter of the ratio of ion charge mobilities in the bipolar diffusion charger. The circuit may comprise a hardware processor. Typically, the sensor comprises an ion trap between the bipolar diffusion charger and the at least one said electrometer, configured to remove free (e.g. flowing) positive and negative ions, which have been mixed with the received particles (in the bipolar diffusion charger), from the resulting mixture of particles and positive and negative ions, before the received particles reach at least one said electrometer. The sensor is used with a gas sample comprising particles of a known diameter and number concentration profile.

Furthermore, in a fourth aspect, the invention extends to a method of measuring the ratio of ion charge mobilities in a bipolar diffusion charger, the method comprising the steps of charging particles of known size and/or concentration in a gas sample by bipolar diffusion charging, using a bipolar diffusion charger, thereby charging the particles by the collision of received particles with and the transfer of charge from both positive and negative ions concurrently, using at least one electrometer to detect the net charge of particles which are thereby charged and processing the measured current to determine the ratio of ion charge mobilities within the bipolar diffusion charger.

Typically, the method comprises removing free positive and negative ions (formed during bipolar diffusion charging, e.g. from collisions between gas molecules and radiation) from the mixture of received particles and positive and negative ions formed during bipolar diffusion charging, using an ion trap (which removes the positive and negative ions from the mixture), before the received particles reach at least one said electrometer. The positive and negative ions may be removed (from the received particles) before the received particles reach at least one said electrometer. It is possible for the ion trap to be an electrometer. In this case, the ions are typically removed by the ion trap and the charge of the received particles is detected by at least one further electrometer. The method comprises measuring or taking into account a known rate of gas flow through the bipolar diffusion charger.

It may also be that some or all of the positively or negatively charged particles are separated from particles of different and/or opposite polarity, for example the positively charged received particles and the negatively charged received particles are separated. The charge of the separated positively charged particles and/or the charge of the separated negatively charged particles, may be measured. In this case only size or concentration are required to be known. Where only the net charge of charged received particles is measured, typically both size and concentration (i.e. first moment of particle size distribution) are required to be known.

Further optional features of the third and fourth aspects of the invention correspond to those discussed above in relation to the first and second aspect of the invention.

DESCRIPTION OF THE DRAWINGS

An example embodiment of the present invention will now be illustrated with reference to the following Figures in which.

DETAILED DESCRIPTION OF AN EXAMPLE EMBODIMENT

First Example—Measuring Net Aerosol Current

Figure 1:
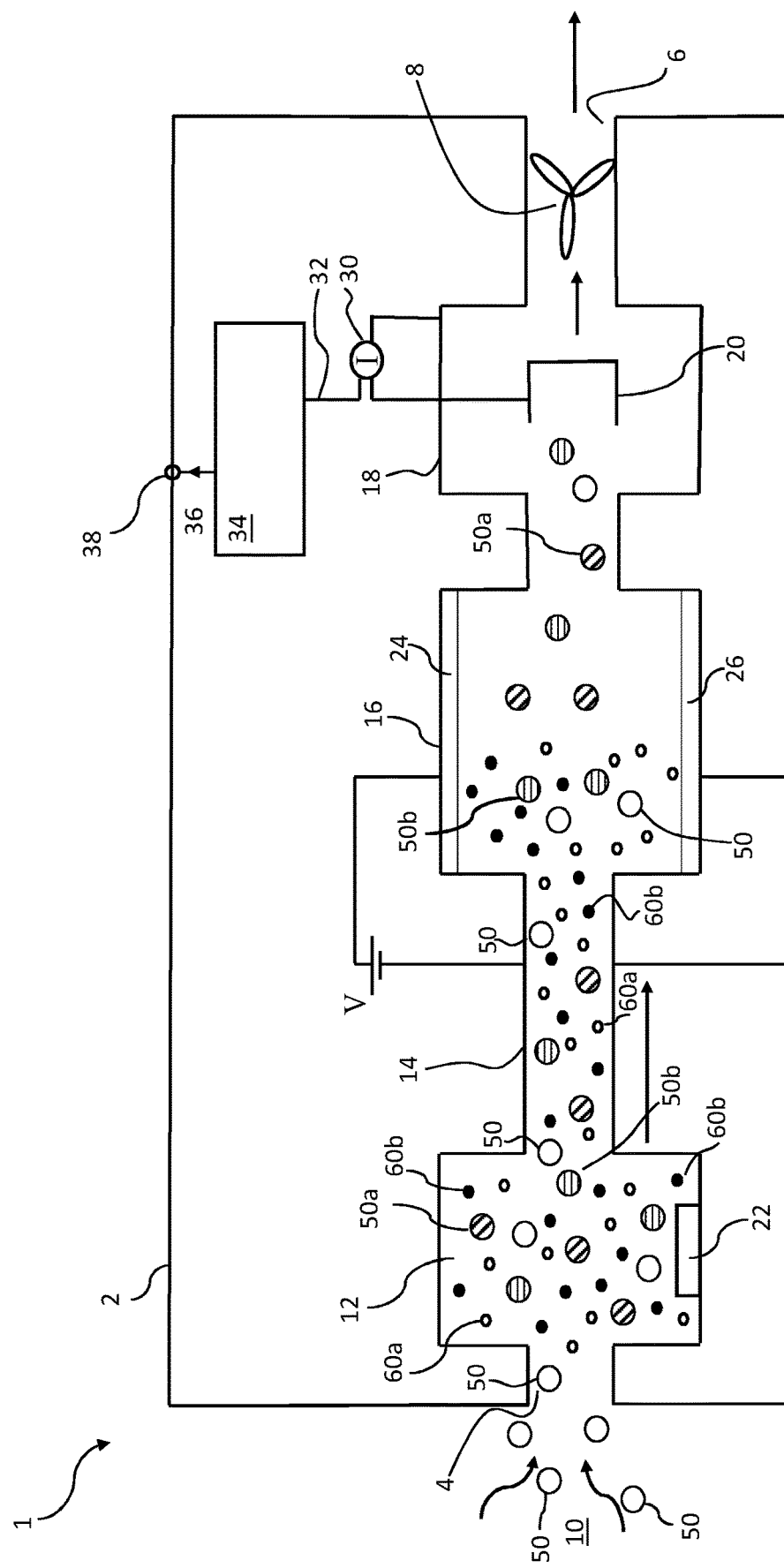
FIG. 1 is a schematic diagram which is not to scale of a flow-through particle sensor according to a first example of the invention.

With reference to FIG. 1, a first example of particle sensor 1 has a body 2 defining an inlet 4 and an outlet 6. A fan 8 is configured to draw an air sample 10 along an air flow path in use, through a chamber which functions as a bipolar diffusion charger 12, a conduit 14, which extends from the bipolar diffusion charger to an ion trap 16, and then to a particle detection chamber 18 which comprises a Faraday cup 20, functioning as an electrometer.

The invention is for analysing particles 50, 50a, 50b within an air sample 10 (the received particles). Particles are shown schematically and not to scale. In FIG. 1, neutrally charged particles 50 are shown with an open circle, a diagonally striped circle indicates a positively charged particle 50a and a circle with horizontal lines indicates a negatively charged particle 50b. Although the Figures show only neutrally charged particles at the inlet, in practice ambient air includes some charged particles and/or free gas ions. Therefore some received particles may already be charged, with a charge distribution which depends on, inter alia, their source and age. However, the equilibrium processes of bipolar diffusion charging will mean that variations in the charge distribution in received particles will, unless highly charged, have negligible effect.

The bipolar diffusion charger 12 includes an ionizing radiation source 22, which in an example is formed by three units of Americium-241 (alpha decay, 432.2 year half life), spaced apart along a flow chamber, and with a combined activity of under 111 kBq, and in another example is formed by Krypton-85 (beta decay, 10.76 years half life), 370 MBq.

The ion trap takes the form of a flow-through electrostatic precipitator which has opposed and oppositely charged electrodes 24, 26 and a circuit configured to maintain a potential difference between these electrodes in use. The electrometer comprises a current sensor 30, having an output 32 which is connected to an input of a controller 34 which in turn has a signal output 36 extending to an output interface 38. The controller typically comprises a processor (such as a microprocessor or microcontroller) executing stored code although its function may be implemented in whole or part with discrete electronic components.

In use, the air sample comprising uncharged particles 50 which are to be analysed, is drawn through the sensor by the action of the fan, into the bipolar diffusion charger 12. Ionizing radiation from the radiation source 22 ionises gas molecules to form a mixture of positively charged gas ions 60a and negatively charged gas ions 60b. Overall, these gas ions within the bipolar diffusion charger have a net zero charge. No electrical potential gradient is applied within the bipolar diffusion charger and the ions move by diffusion and by virtue of electrostatic forces (between charged particle and ions rather than by virtue of an externally applied electric field). The particles in the flowing gas (the received particles) sample collide with the positively and negatively charged ions and become charged so that there are concurrently formed both positively and negatively charged particles (50a, 50b). Some particles continue to have, or regain, a net charge of zero. As particles flow through the conduit, the charge distribution continues to tend to an equilibrium. As we will explain further below, the net result of this bipolar diffusion charging is that the individual particles have a statistical distribution of charges but with an overall net negative charge. Bipolar diffusion charging uses a mixture of both positive and negative ions and the diffusion of these ions to charge particles, obtaining a mixture of positive and negative ions concurrently.

Within the ion trap, the potential difference applied between the electrodes 24, 26 is selected to be sufficient to cause the free gas ions 60a, 60b which remain in the flowing gas sample to be drawn to the electrodes and therefore separated from the particles 50, 50a, 50b. This is readily achieved by selection of an appropriate potential gradient as the particles 50, 50a, 50b typically have a substantially lower mobility than the gas ions 60a, 60b, usually by a factor of at least 100 for particles with a diameter of 10 nm (and a greater factor for larger particles). The particles 50, 50a, 50b, without the gas ions, continue to flow towards the detector 18.

Within the detector 18, a Faraday cup electrometer 20 collects all of the particles, including the neutral particles, using a high-efficiency particulate air (HEPA) filter. The flux of charged particles into the electrometer induces an image current on the Faraday cup, which is measured by the ammeter 30. Air, which is generally free of particles, passes out of the outlet 6.

The controller 34 processes the measured current and the air speed to calculate a value of the first moment of the particle diameter distribution per unit volume, or a related property such as lung deposited surface area per unit volume, which it outputs as a digital or analogue signal throughout output 38. If the speed of rotation of the fan 8 is sufficiently controlled, the speed of air flow may be known, and a constant scaling factor may be employed. Alternatively, an anemometer or other air flow sensor may be used to measure air flow velocity. In some embodiments, no fan is present, either because air is drawn or pushed through the filter at a known speed, or it is judged sufficient to measure the speed of air flow.

The invention exploits several properties of the equilibrium charge distribution arising from bipolar diffusion charging. By way of explanation, at bipolar charge equilibrium, the fraction of total particles ($f_q$) at each charge state (q) as a function of diameter greater than 50 nm is estimated as follows by Gunn R. and Woessner R. (Measurement of the systematic electrification of aerosols, *Journal of Colloid Science*, 1956, 11, 254-259):

$$f_q(d) = \frac{e}{\sqrt{2\pi G}} \exp\left(-\frac{(q - Ge^{-2}\ln(Z_+/Z_-))^2}{2Ge^{-2}}\right) \quad (1)$$

where $$G = 2\pi\varepsilon_0 dkT \quad (2)$$

for a given absolute temperature (T), positive to negative ion mobility ratio ($Z_+/Z_-$), and the constants of electron charge (e), vacuum permittivity ($\varepsilon_0$) and Boltzmann's constant (k). The mean charge per particle ($\bar{q}_d$) for a given particle diameter (d) is given as the sum:

$$\bar{q}_d = \sum_q q f_q(d) \quad (3)$$

and the corresponding current as a function of diameter ($i_d$) is:

$$i_d = Q e N_d \bar{q}_d \quad (4)$$

Where Q is the volumetric flow rate of the gas containing the charged aerosol and $N_d$ is the number concentration of particles of diameter, d. The summation over the discrete charge states of Equation 4 requires a numerical calculation which can be analytically approximated as shown in Equation 5.

$$\bar{q}_d = \int q f_q(d) dq,$$
$$\bar{q}_d = \frac{i_d}{N_d Q e} = \frac{2\pi\varepsilon_0 kT}{e^2} \ln\left(\frac{Z_+}{Z_-}\right) d. \quad (5)$$

Figure 2:
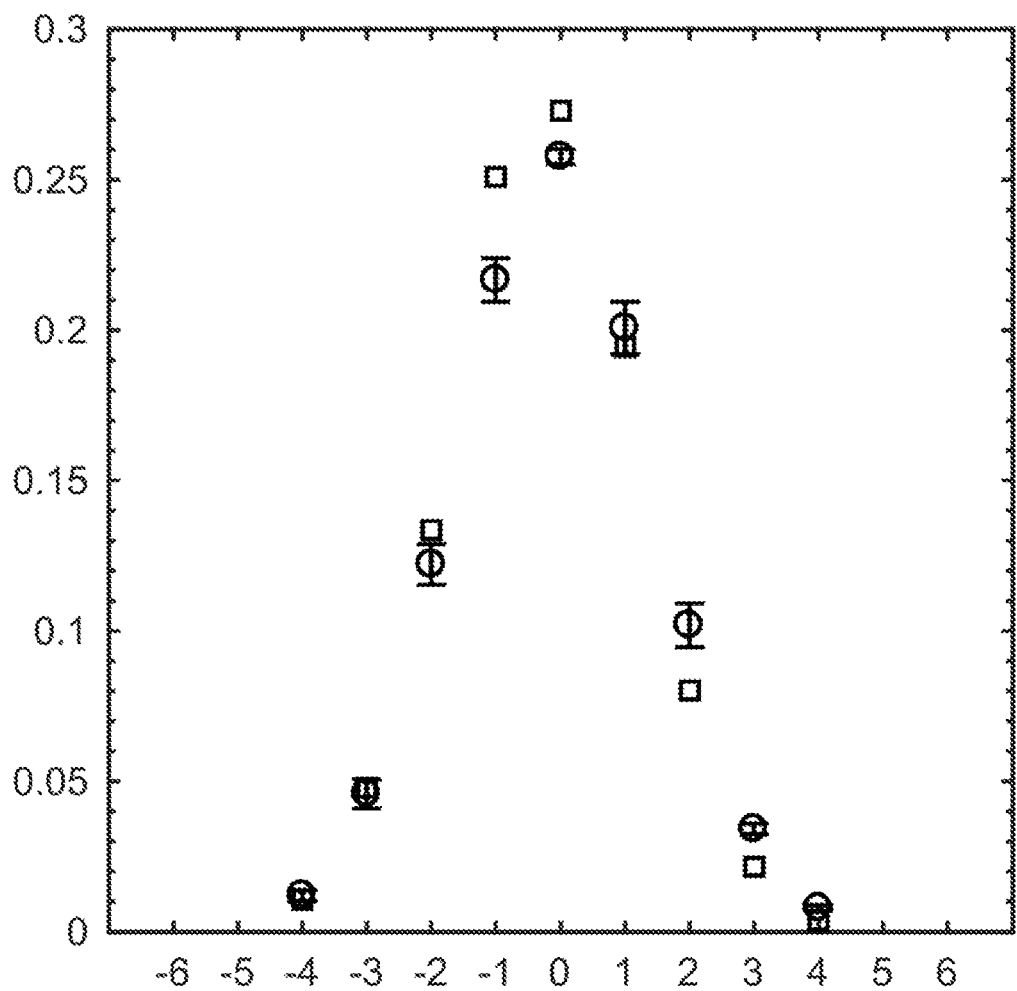
FIG. 2 is a plot of the fraction of particles (y-axis) which have a given charge state (x-axis), expressed as a multiple of the elementary charge, e, following bipolar diffusion charging, both in an experiment (circles) and in theory (squares)

At standard conditions the largest difference between the integral approximation (Eq. 5) and the discrete charge summation (Eq. 3) is 0.5%. This disagreement occurs for particles of 50 nm, which is about the minimum size for which these particular equations are valid, although the sensor is useful for measuring smaller particles too. FIG. 2 shows the high correlation between theory and measured charge states in an example.

Equation 5 states that the mean charge per particle ($\bar{q}_d$) and corresponding net current ($i_d$) for a given particle diameter (d) is a simple linear function of the particle diameter (d), the gas temperature (T), and the natural log of the ratio of positive to negative ion mobilities ($Z_+/Z_-$). The mean charge ($\bar{q}$) carried by an aerosol with a polydispersed distribution of particle sizes is given by the integral sum of all electrical charges over all diameters, given by the distribution $f_d$:

$$\bar{q} = \int_0^\infty \bar{q}_d(d) f_d(d) dd. \quad (6)$$

The corresponding net aerosol current can be derived therefrom as:

$$i = \left[Qe\frac{2\pi\varepsilon_0 kT}{e^2}\ln\left(\frac{Z_+}{Z_-}\right)\right]N\bar{d}. \quad (7)$$

where $\bar{d}$ is the mean particle diameter of the polydispersed aerosol. Note $\bar{q}$ is the mean charge per particle over a polydisperse distribution whereas $\bar{q}_d$ (of Eq. 5) is the mean charge per particle at one particle size.

From Equation 7, it is clear that the only knowledge required to determine Nd is the measured current, the gas flow rate and temperature, and the ratio of ion mobilities. The former can be measured accurately, while the latter can be determined for common mixtures. The net current detected at the Faraday cup electrometer will therefore be approximately proportional to Nd for a range of particle diameters and accordingly the current may be used to estimate the LDSA concentration of aerosols within the received sample.

The particle sensor may therefore also be useful for measuring the net ratio of ion mobilities in a bipolar charger. For particles of a known size and concentration, the net ratio of ion mobilities in the bipolar charger can be calculated from the measured current, taking into account known or measured gas flow rate and known or measured temperature, using Equation 7. In this application, particles with a known size distribution and so known Nd are passed through a bipolar diffusion charger at a known or measured volumetric flow rate, at a known or measured temperature (and possibly humidity) and the measured current is processed to calculate the net ratio of ion mobilities within the bipolar diffusion charger. The resulting ratio is useful in a number of applications, for example it may be used to correct equilibrium charge states for use in the SMPS inversion algorithm for multiple-charge correction an SMPS devices. The ratio may be calculated to determine the effects of changes in gas composition on the ratio of ion mobilities.

Figure 3:
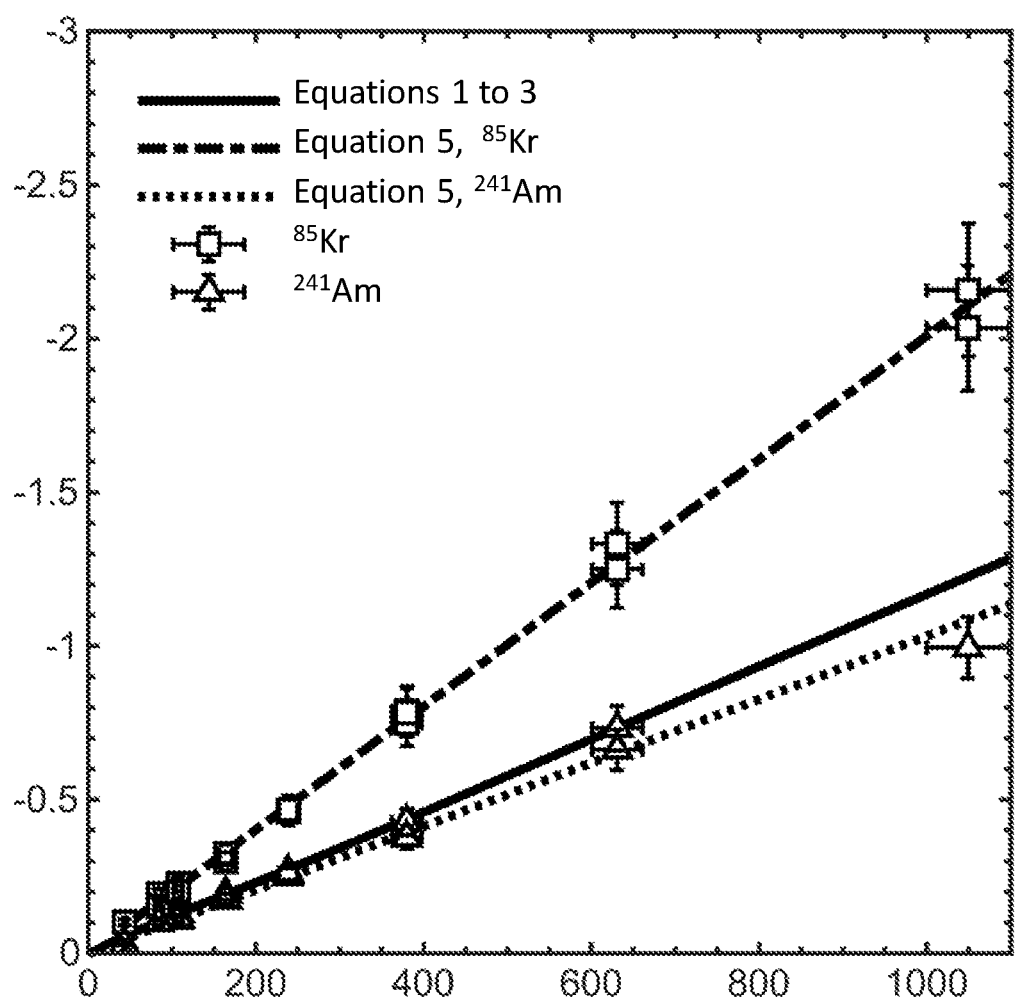
FIG. 3 is a graph of the mean charge per particle (expressed as a multiple of the elementary charge, e, versus particle diameter, in an experiment using sources of Kr-85 (squares) or Am-241 (triangles), and also as predicted from theory using the Fuchs equilibrium, using Equations 1 to 3 ($f_q$ from Gunn & Wiedensholer using $Z_+/Z_-=0.875$) (solid line); using Equation 5, for Kr-85 (Gunn approximation using $Z_+/Z_-=0.795$) (dashed and dotted line); and using Equation 5, for Am-241 (Gunn approximation using $Z_+/Z_-=0.889$) (dotted line)

FIG. 3 demonstrates that in a practical embodiment, the mean charge per particle obtained using the radiation sources described above is a linear function of particle diameter, as predicted from theory, from about 50 nm to about 1000 nm. The relationships remain reasonably accurate below and above this range. Eventually, for sufficiently large particles, it is overtaken by other effects.

Spherical particles (Bis(2-ethylhexyl) sebacate; DOS) were atomized using a nebulizer with HEPA-filtered, compressed air. A sample from the main flow of spherical particles was diluted using a disk diluter to provide a range of particle number concentrations (dilution ratios between 10 and 150), while the remaining aerosol was vented. A custom-built electrostatic precipitator (ESP) removed any particles charged during atomization or dilution. The diluted aerosol sample was then classified by an aerodynamic aerosol classifier to generate an aerodynamically monodispersed source. Since the DOS formed nano-droplets (i.e. spherical particles of known density), the AAC classified particles were also monodispersed in particle geometric diameter which was calculated at each AAC setpoint. It should be noted that for spherical particles this geometric diameter is equivalent to the particle mobility diameter, a parameter commonly used by others to validate bipolar and unipolar diffusion charging theory (Gopalakrishnan, R.; Thajudeen, T.; Ouyang, H.; Hogan Jr, C. J. The unipolar diffusion charging of arbitrary shaped aerosol particles. Journal of Aerosol Science 2013, 64, 60-80; and Gopalakrishnan, R.; McMurry, P. H.; Hogan Jr, C. J. The bipolar diffusion charging of nanoparticles: A review and development of approaches for non-spherical particles. Aerosol Science and Technology 2015, 49, 1181-1194.)

The neutral, monodispersed particles were sampled by a condensation particle counter (CPC) to measure particle number concentration (N) in parallel with the proof-of-concept measurement device. The disk diluter and AAC controlled the particle number concentration and size, respectively. The mean charge per particle can be determined based on the electrical current measured by the aerosol electrometer operating with flow rate (Q) and total particle number concentration (N) using Equation 5. This mean charge per particle (q) is compared against the one predicted by theory using Equation 5 with the total particle number concentration (N) measured by the CPC and the mean particle diameter selected by the AAC (d).

Figure 4:
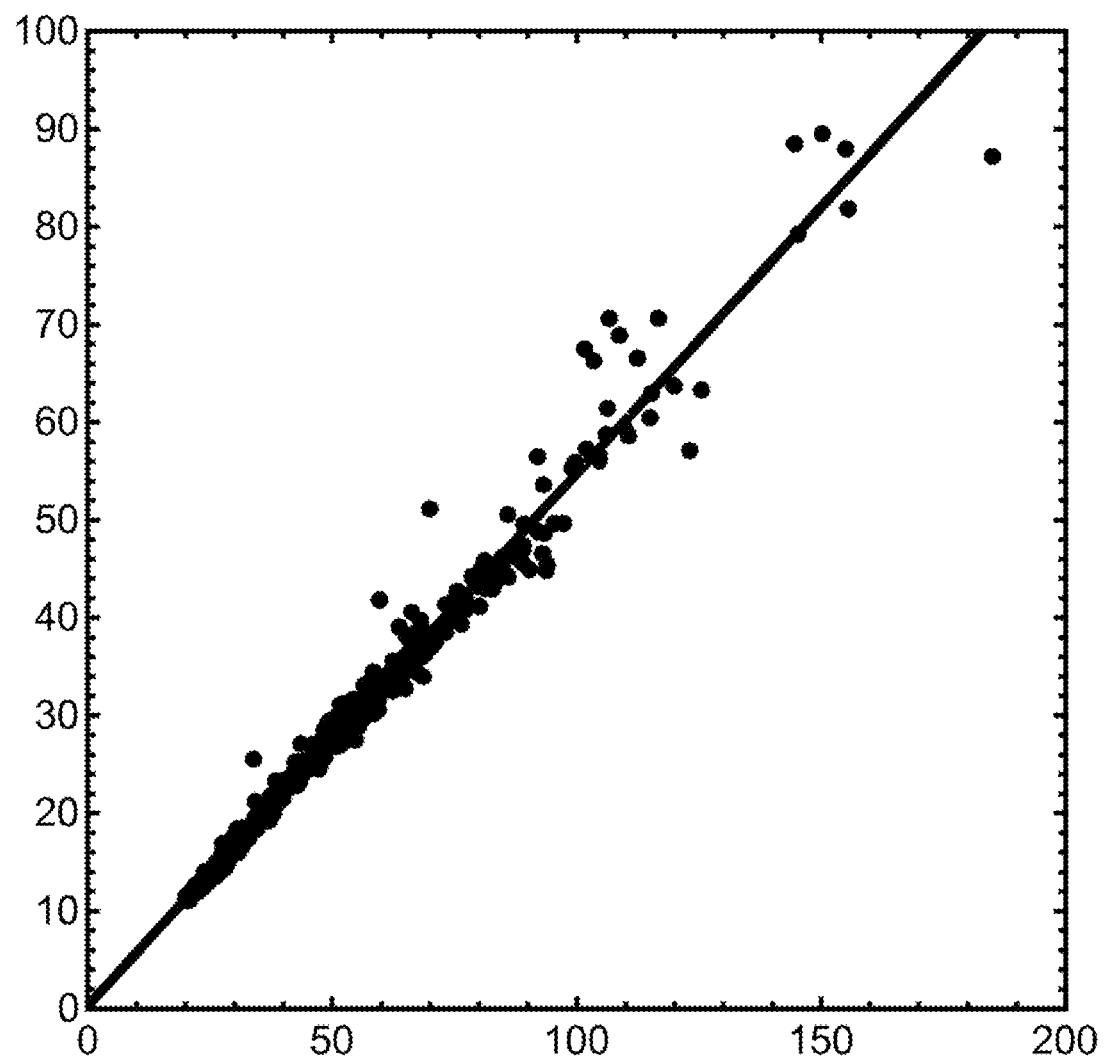
FIG. 4 shows, on the y-axis, the output current from the electrometer of an experimental sensor according to the invention versus, on the x-axis, the output signal from a reference instrument, for measurements taken over a time range and in the same place in an urban environment.
Figures 5A, 5B, 5C:
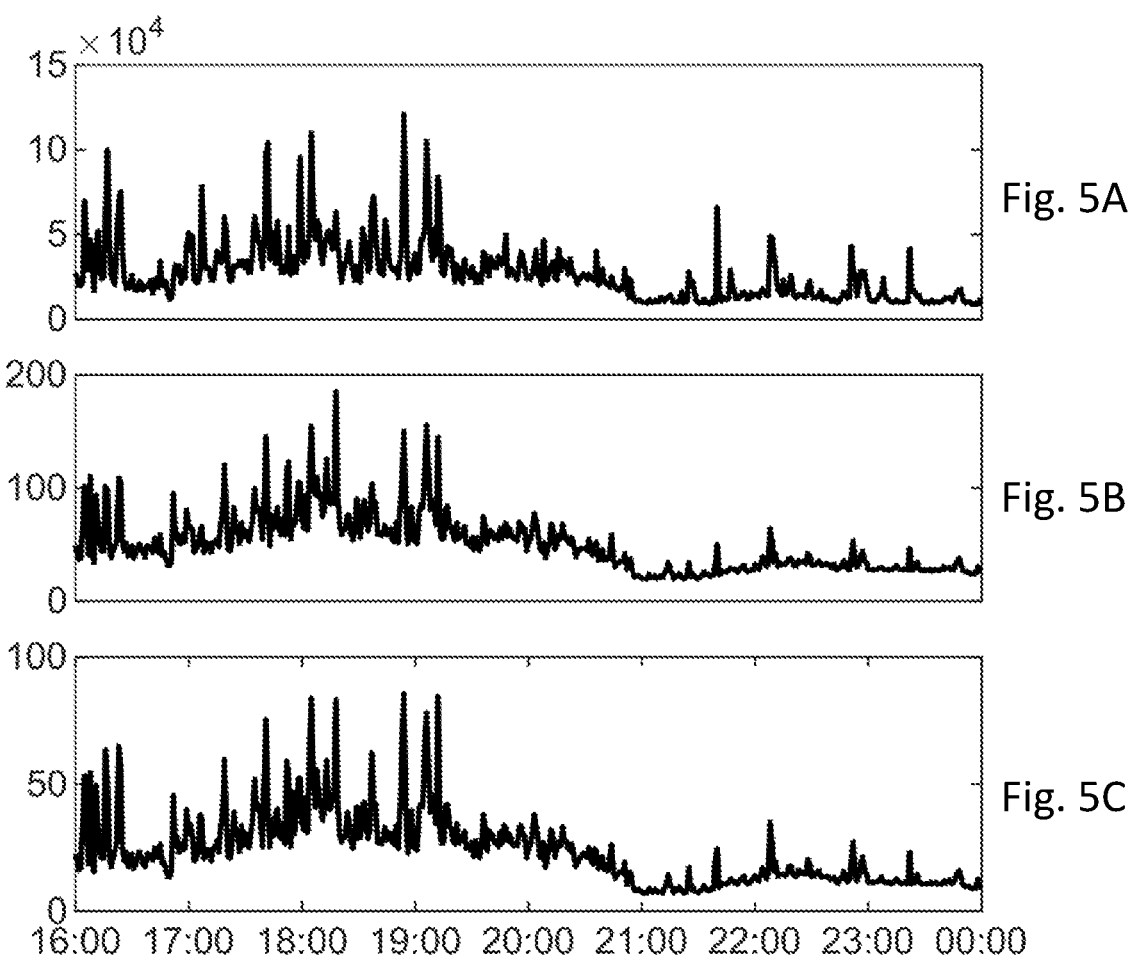
FIGS. 5A through 5C shows on the x-axis the time of day and on the left hand y-axis measurements in FIG. 5A of particle count N ($cm^{-3}$), in FIG. 5B of LDSA ($\mu m^2/cm^3$), and in FIG. 5C of aerosol current, I (fA), for measurements taken over a time range and in the same place in an urban environment using in FIG. 5A a condensation particle counter (N), FIG. 5B a reference device (LDSA), and in FIG. 5C a device according to the present invention (i)

FIG. 4 shows the current obtained from the detector of a prototype device according to the present invention in comparison with a Naneos Partector reference instrument which is considerably more expensive than a sensor as described herein would cost (Naneos and Partector are trademarks of Naneos Particle Solutions GmbH, Windisch, Switzerland). FIGS. 5A, 5B and 5C show the output signal for measurements made near an urban road over time in FIG. 5A, particle count information from a condensation particle counter (number concentration in units of particles per cubic centimetre), FIG. 5B, the Naneos Partector (LDSA in units micrograms per cubic meter) and FIG. 5C, a prototype device for the present embodiment (current in units of femtoAmps, which is proportional to LDSA).

It can be seen that the detector according to the invention has an output which correlates closely with the reference device but in a simple product which can be manufactured at low cost. The output current is proportional to the first moment of particle size distribution and can therefore be used to estimate lung deposited surface area, whereas the reference device measures an output signal approximately proportional to the first moment of particle size distribution, subject to more environmental variables. The device can be substantially miniaturised, with the practical size of electronics likely to be the limiting size consideration. The radiation sources are comparable to or may be the same as those used in everyday smoke alarms and do not require special handling procedures for consumers. In contrast to, for example ionisers based on corona discharges, no ozone or other environmentally damaging gases are produced.

The invention may use any bipolar ion source which produces an equilibrium charge distribution on particles. Embodiments for use in environments with high particle concentrations, or where high sample flow rates are required, may require ion sources which produce a greater excess of ions. Nevertheless, it is not essential that the bipolar charging of the particles actually reaches a steady state. Where insufficient ions are produced, or the particle residence time is too short (e.g. due to a high air speed), a steady state (equilibrium) might not be reached, but there will be a functional relationship between particle charge and mean diameter and concentration.

An important feature of the invention is that the net charge on particles is relatively stable and, provided that an excess of ions is generated, is insensitive to variations in the rate of ion generation and the residence time of particles exposed to ions (in contrast to unipolar ion chargers, for example), provided they are above a minimum threshold. Accordingly, the embodiment described above with reference to FIG. 1 does not require to include any means of measuring or controlling the rate of ion generation.

Nevertheless, in some embodiments, the current which flows between the electrodes, 24, 26, could be measured and used as an indicator as to when a steady state is not being reached. For example, in this case, the current generated from the capture of ions at either of the opposed electrodes would be lower than anticipated. This could be used to determine that the ion source is no longer functioning effectively. However, a decrease in the ion current over a relatively short period of time may indicate that there is an excessively high concentration of particles present. This could be useful to indicate that the device may not provide an accurate reading, or to provide a smoke detector function or an alarm for a high concentration of aerosols.

It is also possible to determine when the charge equilibrium is not being adequately achieved from the current at the one or more electrometers. If the first moment of particle size distribution (Nd) exceeds a threshold the total current will level out as there will be insufficient ions to enable equilibration for the particles which are present. Accordingly, an alert can be generated responsive to the current at the one or more electrometers exceeding a predetermined threshold.

Where required, the sensitivity of the device can be improved by employing modulation. For example, the ion trap might be switched on and off according to a predetermined pattern, e.g. square wave, and the resulting modulation detected in the current measured at the electrometer. It would also be possible to modulate the ion source, for example with a shutter or gate between the radioactive element and the bulk of the volume of the bipolar diffusion chamber.

Second Example—Separation of Positively and/or Negatively Charged Particles

Figure 6:
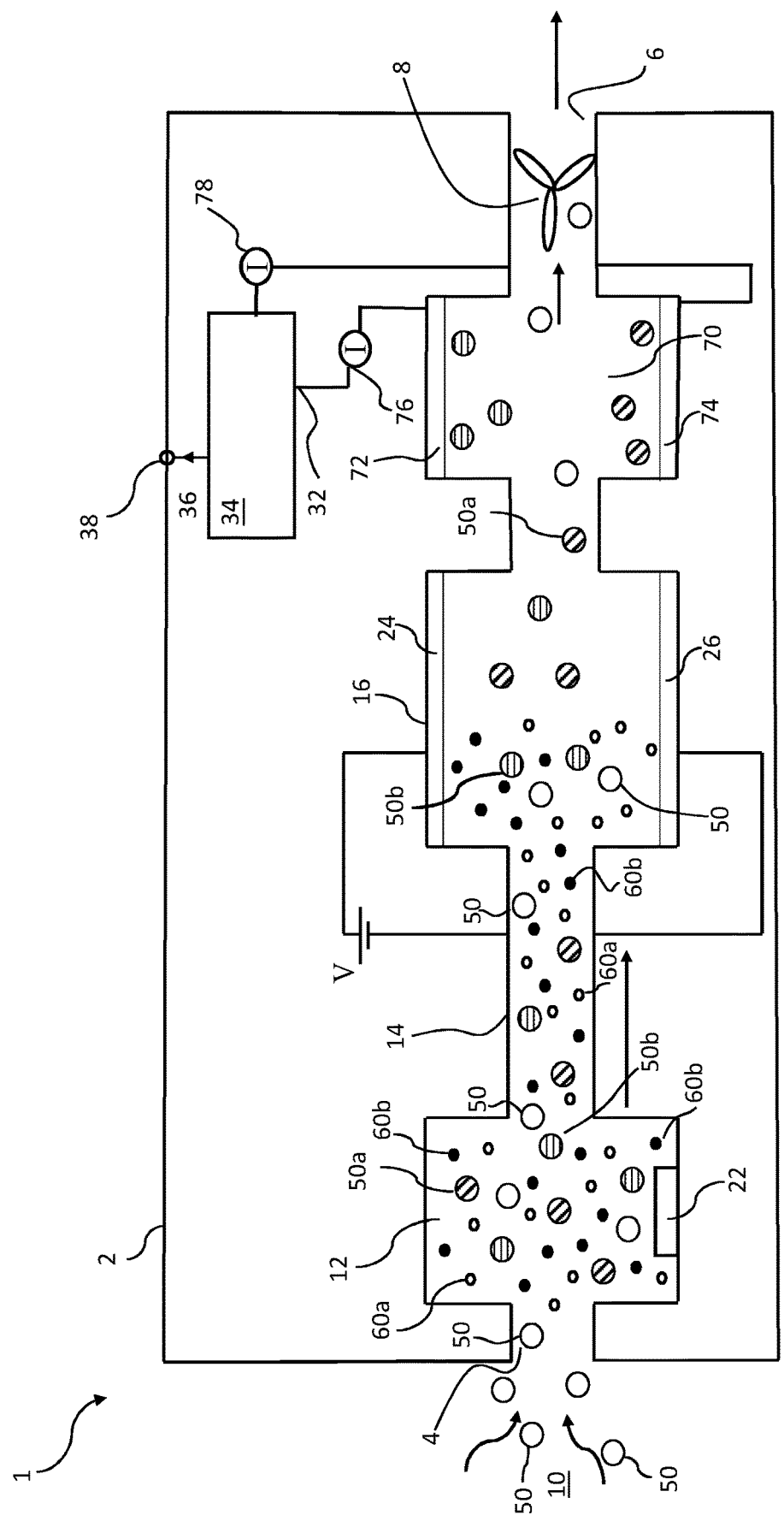
FIG. 6 is a schematic diagram of a second embodiment of the invention.

In a second example embodiment, illustrated with reference to FIG. 6, particles which have been charged by bipolar diffusion charging are separated by polarity, i.e. the positive and negative particles are separated from each other. It is not critical whether the neutrally charged particles are, or are not, separated from other particles. Numbered features in FIG. 6 correspond to correspondingly numbered features of FIG. 1. The bipolar diffusion charger 12 and ion trap 16 are as before. However, particle detection chamber 18 and Faraday cup electrometer 20 are replaced with a particle separation and detection chamber 70, which is downstream of the ion trap and which comprise a positively charged electrode 72 and an opposite negatively charged electrode 74. First and second ammeters 76 and 78 measure the current in each electrode in use. The potentials of the positively charged and negatively charged electrodes are selected to cause positively charged particles 50b to be captured by the negatively charged electrode 74, and their charge detected by the second ammeter, giving a current $i_+$, while the negatively charged particles 50a are captured by the positively charged electrode 72 and their charge detected by the first ammeter, giving a current L. Neutrally charged particles pass through the chamber and the outlet 6. As apparent from FIG. 2, the positively charged particle current, $i_+$, comprises contributions from particles having each of a plurality of different positive charges, and the negatively charged particle current, $i_-$, comprises contributions from particles having each of a plurality of different negative charges.

The controller 34 processes $i_+$ and $i_-$ to determine size parameters of the particles, including the LDSA and/or first moment of the size distribution (Nd) of the particles, with reference to calculated or calibrated equivalence data representing the relationship between these currents, and number concentration and size parameters. The controller may calculate abs $[i_+]$+abs$[i_-]$ (abs referring to the absolute value of), referred to herein as the total aerosol current and/or abs $[i_+]$−abs $[i_-]$, the net aerosol current, which corresponds to the current which would be measured using the first example sensor.

Following a similar derivation to predict the net mean charge per particle (Eqn 5) of the first embodiment, the mean charge per particle for positively ($\bar{q}_{d_+}$) or negatively ($\bar{q}_{d_-}$) charged particles of given diameter (d) separated and measured by the second embodiment can be estimated using:

$$\bar{q}_{d+} = \int_0^\infty q \cdot f_q dq = \frac{\sqrt{G}}{e\sqrt{2\pi}}\exp(-C^2) + \frac{G}{2e^2}\cdot\ln\left(\frac{Z_+}{Z_-}\right)\text{erfc}[-C] \quad (7)$$

$$\bar{q}_{d-} = \int_{-\infty}^0 q \cdot f_q dq = -\frac{\sqrt{G}}{e\sqrt{2\pi}}\exp(-C^2) - \frac{G}{2e^2}\cdot\ln\left(\frac{Z_+}{Z_-}\right)(-2+\text{erfc}[-C]) \quad (8)$$

where G is defined by Eqn 2 and C is:

$$C = \frac{\sqrt{G}}{e\sqrt{2}}\ln\left(\frac{Z_+}{Z_-}\right). \quad (9)$$

These mean charge per particle based on particle polarity correspond to the following aerosol currents as a function of particle diameter:

$$i_{d+} = QeN_d\bar{q}_{d+} = QeN_d\left(\frac{\sqrt{G}}{e\sqrt{2\pi}}\exp(-C^2) + \frac{G}{2e^2}\cdot\ln\left(\frac{Z_+}{Z_-}\right)\text{erfc}[-C]\right) \quad (10)$$

$$i_{d-} = QeN_d\bar{q}_{d-} = QeN_d\left(-\frac{\sqrt{G}}{e\sqrt{2\pi}}\exp(-C^2) - \frac{G}{2e^2}\cdot\ln\left(\frac{Z_+}{Z_-}\right)(-2+\text{erfc}[-C])\right) \quad (11)$$

Figure 7:
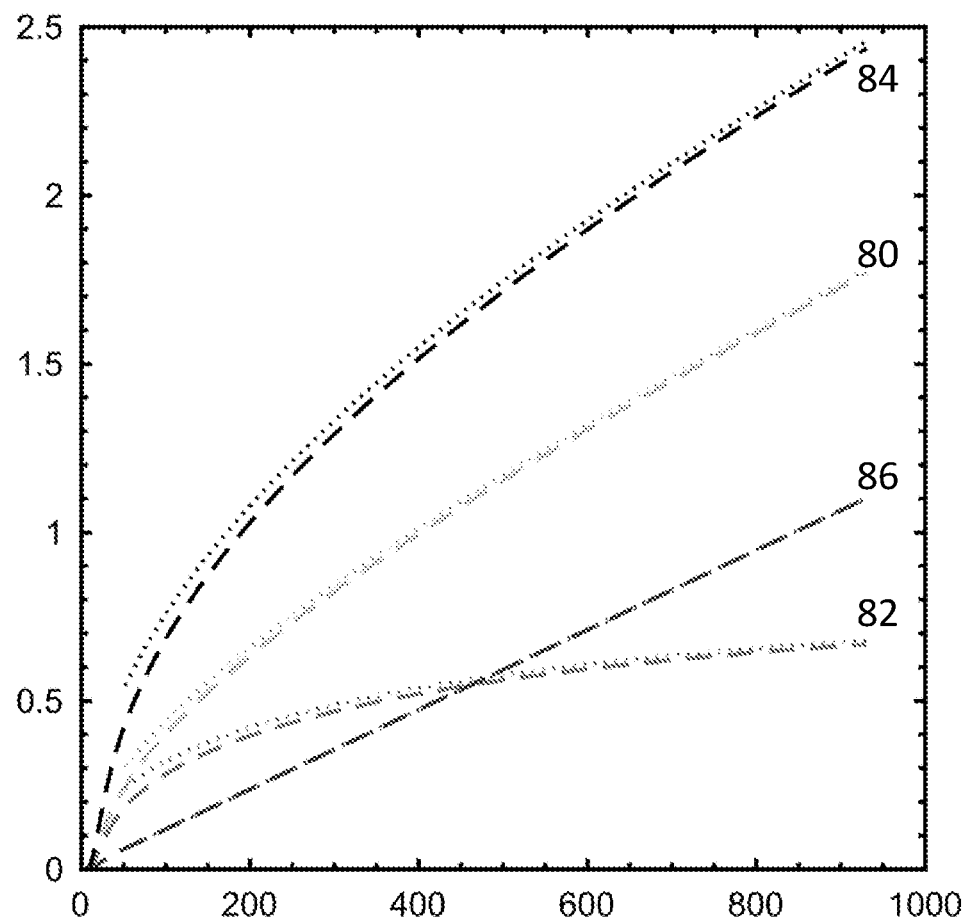
FIG. 7 is a graph of the calculated expected absolute values of (i) the mean charge per particle for positively charged particles (82), (ii) the mean charge per particle for negatively charged particles (80), (iii) the difference between (i) and (ii) (the net mean charge per particle) (86) and the sum of (i) and (ii) (the total mean charge per particle) (84) in particles charged by a bipolar diffusion charger at standard conditions, versus particle diameter.

FIG. 7 shows the predicted magnitude of the mean charge per particle from different components of the aerosol sample assuming gas at standard conditions as a function of different particle diameters; specifically the magnitude of the mean charge per particle for positively charged particles, $\bar{q}_+$ 82, the magnitude of the mean charge per particle for negatively charged particles, $\bar{q}_-$ 80, the sum of these, the total mean charge per particle, abs $[\bar{q}_+]$+abs $[\bar{q}_-]$, 84, and the magnitude of the difference between the positively charged particle and the negatively charged particles, the net mean charge per particle, abs $[\bar{q}_+]$−abs $[\bar{q}_-]$, 86. In each case, dashed lines are numerical solutions predicted by Gunn & Wiedensohler, and the dotted lines are an analytical solutions derived from Gunn to approximate the numeric solutions. This figure is an expansion of FIG. 3 which only shows the net mean charge per particle.

Figure 8:
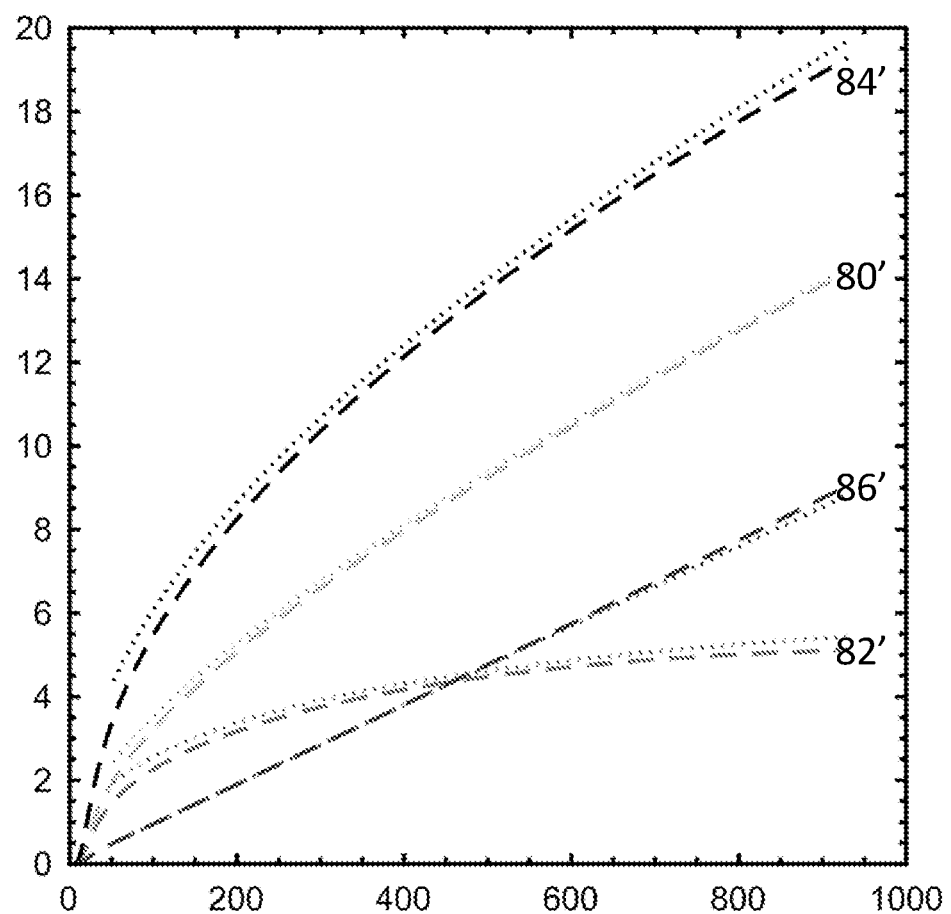
FIG. 8 is a graph of the calculated expected absolute values of (i) the current for positively charged particles (82'), (ii) the current for negatively charged particles (80'), (iii) the difference between (i) and (ii) (the net aerosol current) (86') and the sum of (i) and (ii) (the total aerosol current) (84') in particles charged by a bipolar diffusion charger versus particle diameter, assuming 10,000 particles per cubic centimetre of gas at standard conditions with a sample flow-rate of 0.3 L/min.

FIG. 8 shows the predicted magnitude of the currents from different components of the aerosol sample assuming 10,000 particles per cubic centimetre of gas at standard conditions with a sample flow-rate of 0.3 L/min as a function of different particle diameters; specifically the positively charged particle current, $i_+$, 82', the negatively charged particle current, $i_-$, 80', the sum of these, the total aerosol current, abs $[i_+]$+abs $[i_-]$, 84' and the magnitude of the difference between the positively charged particle current and the negatively charged particle current, the net aerosol current, abs $[i_+]$-abs $[i_-]$, 86'. In each case, dashed lines are numerical solutions predicted by Gunn & Wiedensohler, and the dotted lines Whereas FIG. 7 shows the absolute mean charge per particle (abs[$\bar{q}$]), FIG. 8 shows the corresponding aerosol current (i) assuming a particle concentration and sample flow-rate.

It can be seen that the positively charged particle current, the negatively charged particle current, and the total aerosol current are each substantially larger than the net aerosol current, abs $[i_+]$-abs $[i_-]$, particularly at lower particle diameters. We calculate that the ratio of total aerosol current to net aerosol current would be about 1900% for 2 nm diameter particles. This increase in measurable current may greatly improve measurement accuracy, particularly at low particle sizes where currents are smallest and prone to error.

Still further, as two independent current measurements are made, the controller 34 can independently calculate the number density of particles (N) and their mean diameter ($\bar{d}$), rather than only the first moment of the particle size distribution. The independent currents may have different properties, for example the positively charged particle current, $i_+$, is much less sensitive to particle size than the negatively charged particle current, $i_+$. Thus the positively charged particle current, $i_+$, alone might give a useful indication of particle concentration within a range of uncertainty. This is relevant for example to periodic technical inspection requirements in Germany which allow a relatively high uncertainty for number concentration measurements.

In the above example, all positively charged particles are separated from all negatively charged particles. However, it would suffice to separate positively charged particles having at least a threshold electrical mobility or negatively charged particles having at least a threshold electrical mobility from particles of the opposite charge (and typically also from the neutrally charged particles), for example by applying an offset to the potential of both electrodes 72, 74, and in some circumstances this would provide additional information.

It is alternatively possible to measure the positive and negative particle currents $i_+$ and $i_-$ using apparatus like that of FIG. 1 further including a trap which can selectively remove positive or negative particles, enabling the measurement of the charge of the remaining particles, which is modulated in use. Alternatively, positively and negatively charged particles may be separated using an electromagnetic field and detected by separate electrometers 20.

In the examples above, ions are formed in air molecules with properties and in a ratio which depends on the type and energy of radioactive decay as well as the state and composition of the carrier gas, which affects the net particle charge for a given diameter. In some embodiments, the properties of the ions in the bipolar diffusion charger are manipulated. One way in which this can be achieved is to introduce new components to the received gas, either before the sample gas reaches the bipolar diffusion chamber, or within the bipolar diffusion charger. It is also possible to vary properties of the charger or the ion source. Changes in the difference between ion mobility for positive and negative charges affect the equilibrium charge distribution of the aerosol, and so one or more components of the gas or properties of the charger or ion source may be selected to increase the signal strength of the device.

In some embodiments, the bipolar diffusion charger comprises a salt such as NaCl or other easily ionisable chemicals (e.g. siloxanes from silicone), which would be preferentially ionised. The presence of these chemicals changes the composition of the ions which are generated, especially the relative mobility of positive and negative ions, and therefore the charge distribution. In some embodiments there is provided a temperature regulator (e.g. heater or cooler) to control the temperature of the ions within the bipolar diffusion charger.

The ion trap may in some embodiments not use an electrical potential gradient, but instead ions may be trapped at walls via Brownian diffusion or electrostatic forces. The ion trap may be an ion selective membrane. These embodiments provide a simpler device.

Further variations and modifications may be made within the scope of the invention herein disclosed.

The invention claimed is:

1. An aerosol particle sensor comprising an inlet for receiving a gas sample for analysis, a bipolar diffusion charger configured to charge received aerosol particles within the received gas sample by the collision of the received aerosol particles with and transfer of charge from both positive and negative ions concurrently, and at least one electrometer configured to detect a charge of received aerosol particles thereby charged, wherein the received aerosol particles are measured by the at least one electrometer without positive and negatively charged aerosol received particles being separated from each other.

2. A particle sensor according to claim 1, wherein the particle sensor comprises an ion trap between the bipolar diffusion charger and the at least one electrometer, wherein the ion trap is configured to remove free positive and negative ions from a mixture of received aerosol particles and positive and negative ions formed in the bipolar diffusion charger, before the received aerosol particles reach the at least one electrometer.

3. A particle sensor according to claim 2, wherein the ion trap comprises a pair of electrodes spaced apart, which are oppositely charged in use, wherein a current generated from a capture of ions at either of the spaced apart electrodes is measured and a controller processes the current to determine one or more parameters of a charge flux in the bipolar diffusion charger, or to detect an excess of aerosol particles.

4. A particle sensor according to claim 2, wherein the ion trap comprises a pair of electrodes spaced apart, which are oppositely charged in use, wherein the current generated from the capture of ions at either of the spaced apart electrodes is measured and the controller processes the current to detect smoke.

5. A particle sensor according to claim 2, wherein the ion trap comprises an electrometer and there is at least one further electrometer downstream of the ion trap.

6. A particle sensor according to claim 2, wherein the ion trap is configured to separate the ions from the received aerosol particles by diffusion.

7. A particle sensor according to claim 1, wherein the particle sensor further comprises a circuit configured to receive signals from the at least one electrometer and calculate at least one parameter of the concentration and/or size of the received aerosol particles in the received gas sample.

8. A particle sensor according to claim 1, wherein charging of the aerosol particles reaches a steady state.

9. A particle sensor according to claim 1, wherein at least some of the received aerosol particles thereby charged, of the same polarity, are separated from aerosol particles of different and/or opposite polarity, before or at the same time as a measurement by the at least one electrometer.

10. A particle sensor according to claim 9, wherein one or more electrometer is configured to both separate at least some of the received aerosol particles, of the same polarity, and to measure the charge of the separated aerosol particles.

11. A particle sensor according to claim 9, wherein the aerosol particles are separated by a potential gradient between electrodes, a potential difference between the electrodes being selected such that the separated aerosol particles have a positive charge, and an electrical mobility higher than a first threshold, or a negative charge, and an electrical mobility higher than a second threshold, and wherein the at least one electrometer measures the separated aerosol particles.

12. A particle sensor according to claim 1, wherein the received aerosol particles are separated by charge polarity prior to a measurement by the at least one electrometer, wherein measurements of a sum of the charge of the separated positively charged aerosol particles and a sum of the charge of the separated negatively charged aerosol particles are both obtained.

13. A method of measuring a parameter of the concentration and/or size of aerosol particles in the gas sample for analysis utilizing the aerosol particle sensor according to claim 1, the method comprising receiving the gas sample comprising the aerosol particles, charging the received aerosol particles in the gas sample by bipolar diffusion charging, thereby charging the received aerosol particles by the collision of aerosol particles with and the transfer of charge from both positive and negative ions concurrently, and using the at least one electrometer to detect the charge of received aerosol particles which are thereby charged.

14. A method according to claim 13, wherein as a result of the bipolar diffusion charging, the received aerosol particles have a net negative charge or a net positive charge and the net charge is measured by the at least one electrometer.

15. A method according to claim 13, wherein the method comprises separating free positive and negative ions from the mixture of received aerosol particles and positive and negative ions formed during bipolar diffusion charging, and wherein the positive and negative ions are removed by an ion trap before the received aerosol particles reach the at least one electrometer.

16. A method according to claim 13, wherein the parameters of charge flux of ions within the bipolar diffusion charger is not measured.

17. A method according to claim 13, wherein the received aerosol particles are separated from the positive and negative ions by an electrical potential gradient applied between electrodes and the current between the electrodes is not monitored.

18. A method according to claim 13, comprising separating some or all of the positively or negatively charged received aerosol particles which have been charged by the bipolar diffusion charger from aerosol particles of different and/or opposite polarity, and measuring the charge of the separated positively and/or negatively charged received aerosol particles.

19. A method according to claim 13, wherein the received aerosol particles are separated by a potential difference applied between two electrodes, and the current at each electrode is measured thereby providing a signal which is a measurement of the charges of the positively charged aerosol particles and a signal which is a measurement of the charges of the negatively charged aerosol particles.

20. A method according to claim 13, wherein the received aerosol particles are separated from the positive and negative ions by an electrical potential gradient applied between electrodes and the current between the electrodes is monitored to measure the rate of ionization or to detect the presence of a concentration of aerosol particles exceeding a threshold or to detect smoke.

21. A method according to claim 13, wherein the charging of the aerosol particles by the positive and negative ions does not reach a steady state.

22. A sensor for the ratio of ion charge mobilities in a bipolar diffusion charger, the sensor comprising an inlet for receiving a gas sample for analysis, a bipolar diffusion charger configured to charge aerosol particles within the received gas sample by the collision of aerosol particles with and transfer of charge from both positive and negative ions concurrently, and at least one electrometer configured to detect a charge of aerosol particles thereby charged, the sensor comprising an ion trap between the bipolar diffusion charger and the at least one electrometer, configured to remove free positive and negative ions from the resulting mixture of received aerosol particles and positive and negative ions before the received aerosol particles reach the at least one electrometer, wherein the received aerosol particles are measured by the at least one electrometer without positive and negatively charged aerosol received particles being separated from each other.

23. A method of measuring the ratio of ion charge mobilities in the bipolar diffusion charger utilizing the sensor according to claim 22, the method comprising the steps of charging particles of known size and/or concentration in the gas sample by bipolar diffusion charging, using the bipolar diffusion charger, thereby charging the particles by the collision of particles with and the transfer of charge from both of the positive and negative ions concurrently, using the at least one electrometer to detect the charge of particles which are thereby charged and processing the measured current to determine the ratio of ion charge mobilities within the bipolar diffusion charger, the method comprising removing free positive and negative ions from the mixture of the received particles and positive and negative ions formed during the bipolar diffusion charging, using the ion trap, before the received particles reach the at least one electrometer.

\* \* \* \* \*